(12) United States Patent
Klemme et al.

(10) Patent No.: US 11,849,280 B2
(45) Date of Patent: *Dec. 19, 2023

(54) APPARATUS AND METHODS FOR BONE CONDUCTION CONTEXT DETECTION

(71) Applicant: Intel Corporation, Santa Clara, CA (US)

(72) Inventors: Beverly Klemme, San Jose, CA (US); Rajashree Baskaran, Portland, OR (US); Sergio E. Sian, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,590

(22) Filed: Jun. 6, 2022

(65) Prior Publication Data

US 2022/0303676 A1 Sep. 22, 2022

Related U.S. Application Data

(63) Continuation of application No. 17/085,884, filed on Oct. 30, 2020, now Pat. No. 11,356,772, which is a
(Continued)

(51) Int. Cl.
*H04R 1/46* (2006.01)
*G10L 21/0232* (2013.01)
(Continued)

(52) U.S. Cl.
CPC ............... *H04R 1/46* (2013.01); *A61B 5/11* (2013.01); *A61B 5/4504* (2013.01); *A61B 5/721* (2013.01);
(Continued)

(58) Field of Classification Search
CPC .... H04R 1/46; H04R 1/1016; H04R 2460/13; H04R 29/001; A61F 11/04;
(Continued)

(56) References Cited

U.S. PATENT DOCUMENTS 4,520,238 A 5/1985 Ikeda
7,269,266 B2 9/2007 Anjanappa et al.
(Continued)

FOREIGN PATENT DOCUMENTS

WO WO-2009141828 A2 * 11/2009 ........... H04R 1/1083

OTHER PUBLICATIONS

Zheng et al., "Air- and Bone Conductive Integrated Microphones for Robust Speech Detection and Enhancement," IEEE Workshop on Automatic Speech Recognition and Understanding, Nov. 30-Dec. 4, 2003, pp. 249-254, 6 pages.
(Continued)

*Primary Examiner* — William A Jerez Lora
(74) *Attorney, Agent, or Firm* — HANLEY, FLIGHT & ZIMMERMAN, LLC

(57) ABSTRACT

Apparatus and methods for bone conduction detection are disclosed herein. An example apparatus includes memory; machine-readable instructions; and processor circuitry to execute the machine-readable instructions to associate a vibration signal with a voice or with motion, the vibration signal transmitted via a bone structure of a user; permit access to a user application based on the association of the vibration signal with the voice; and deny access to the user application based on the association of the vibration signal with the motion.

17 Claims, 9 Drawing Sheets

Related U.S. Application Data continuation of application No. 16/659,050, filed on Oct. 21, 2019, now Pat. No. 10,827,261, which is a continuation of application No. 15/870,043, filed on Jan. 12, 2018, now Pat. No. 10,455,324.

(51) Int. Cl.

| | | |
|---|---|---|
| *H04R 29/00* | (2006.01) | |
| *G10L 25/51* | (2013.01) | |
| *A61F 11/04* | (2006.01) | |
| *G10L 25/78* | (2013.01) | |
| *A61B 5/11* | (2006.01) | |
| *H04R 1/02* | (2006.01) | |
| *A61B 5/00* | (2006.01) | |
| *G10L 21/0208* | (2013.01) | |
| *A61B 5/12* | (2006.01) | |

(52) U.S. Cl.
CPC .......... *A61F 11/04* (2013.01); *G10L 21/0208* (2013.01); *G10L 21/0232* (2013.01); *G10L 25/51* (2013.01); *G10L 25/78* (2013.01); *H04R 1/028* (2013.01); *H04R 29/001* (2013.01); *A61B 5/1123* (2013.01); *A61B 5/12* (2013.01); *A61B 5/4803* (2013.01); *A61B 5/486* (2013.01); *A61B 5/6803* (2013.01); *H04R 2460/13* (2013.01)

(58) Field of Classification Search
CPC ..... G10L 21/0232; G10L 25/51; G10L 25/78; A61B 5/1123; A61B 5/12; A61B 5/4803; A61B 5/486; A61B 5/6803
USPC ................. 381/56, 58, 151, 324, 326, 380
See application file for complete search history.

(56) References Cited

U.S. PATENT DOCUMENTS

| | | | |
|---|---|---|---|
| 8,325,963 B2 | 12/2012 | Kimura | |
| 9,002,020 B1 | 4/2015 | Kim et al. | |
| 9,135,915 B1* | 9/2015 | Johnson ................. | G10L 21/16 |
| 9,173,023 B2 | 10/2015 | Domingo Yaguez et al. | |
| 9,313,572 B2 | 4/2016 | Dusan et al. | |
| 9,324,313 B1 | 4/2016 | Zhong et al. | |
| 9,363,596 B2 | 6/2016 | Dusan et al. | |
| 9,532,131 B2 | 12/2016 | Dusan et al. | |
| 9,620,116 B2 | 4/2017 | Dadu et al. | |
| 9,781,499 B2 | 10/2017 | Kar | |
| 10,097,912 B2 | 10/2018 | Anderson et al. | |
| 10,455,324 B2 | 10/2019 | Klemme et al. | |
| 10,827,261 B2 | 11/2020 | Klemme et al. | |
| 11,356,772 B2 | 6/2022 | Klemme et al. | |
| 2006/0064037 A1 | 3/2006 | Shalon et al. | |
| 2009/0328169 A1 | 12/2009 | Hutchison et al. | |
| 2010/0110368 A1 | 5/2010 | Chaum | |
| 2011/0066041 A1 | 3/2011 | Pandia et al. | |
| 2011/0135106 A1* | 6/2011 | Yehuday ................ | H04R 3/005 |
| | | | 381/151 |
| 2011/0207990 A1 | 8/2011 | Mersky | |
| 2011/0224481 A1 | 9/2011 | Lee et al. | |
| 2012/0330113 A1 | 12/2012 | Kogure | |
| 2013/0072755 A1 | 3/2013 | Papania et al. | |
| 2013/0114835 A1 | 5/2013 | Holmberg | |
| 2014/0337036 A1 | 11/2014 | Haiut et al. | |
| 2015/0179189 A1* | 6/2015 | Dadu ...................... | G10L 15/20 |
| | | | 704/275 |
| 2016/0142817 A1 | 5/2016 | Hotehama et al. | |
| 2016/0286299 A1 | 9/2016 | Anderson et al. | |
| 2016/0379661 A1 | 12/2016 | Kar et al. | |
| 2017/0026744 A1 | 1/2017 | Farzbod et al. | |
| 2017/0086730 A1 | 3/2017 | Lu et al. | |
| 2017/0178668 A1 | 6/2017 | Kar et al. | |
| 2020/0128317 A1 | 4/2020 | Feldman | |

OTHER PUBLICATIONS

Goldendance Co., Ltd., "Bone Conduction: How it Works," Goldendance Co., Ltd., 2008, available at http://www.goldendance.co.jp/English/boneconduct/01.html, last accessed Nov. 10, 2017, 3 pages.

Neovictory, "What is Bone Conduction Technology" available at http://www.neovictory.com/2011/BonSayOn_BoneCo, last accessed Jan. 3, 2018, 2 pages.

Fujita et al., "Marketing a Bone Conductive Receiver/Microphone," NEC Technical Journal, vol. 1, No. 5, 2006, pp. 87-91, 5 pages.

Indiegogo, "CoolRay: Bone Conduction Technology at its Best", available at https://www.indiegogo.com/projects/coolray-bone-conduction-technol- -ogy-at-its-best#/, last accessed May 11, 2017, 11 pages.

United States Patent and Trademark Office, "Non-Final Office Action," issued in connection with U.S. Appl. No. 15/870,043, dated Jan. 24, 2019, 10 pages.

United States Patent and Trademark Office, "Notice of Allowance," issued in connection with U.S. Appl. No. 15/870,043, dated Jun. 12, 2019, 8 pages.

United States Patent and Trademark Office, "Restriction," issued in connection with U.S. Appl. No. 15/870,043, dated Aug. 30, 2018, 5 pages.

United States Patent and Trademark Office, "Non-final Office Action," issued in connection with U.S. Appl. No. 16/659,050, dated Feb. 20, 2020, 6 pages.

United States Patent and Trademark Office, "Notice of Allowance and Fee(s) Due," issued in connection with U.S. Appl. No. 16/659,050, dated Jun. 25, 2020, 7 pages.

United States Patent and Trademark Office, "Supplemental Notice of Allowability," issued in connection with U.S. Appl. No. 16/659,050, dated Oct. 7, 2020, 2 pages.

United States Patent and Trademark Office, "Non-Final Office Action," issued in connection with U.S. Appl. No. 17/085,884, dated Oct. 1, 2021, 10 pages.

United States Patent and Trademark Office, "Notice of Allowance and Fee(s) Due," issued in connection with U.S. Appl. No. 17/085,884, dated Feb. 1, 2022, 7 pages.

* cited by examiner

APPARATUS AND METHODS FOR BONE CONDUCTION CONTEXT DETECTION

RELATED APPLICATIONS

This patent arises from a continuation of U.S. patent application Ser. No. 17/085,884, now U.S. Pat. No. 11,356,772, filed on Oct. 30, 2020. U.S. patent application Ser. No. 17/085,884 is a continuation of U.S. patent application Ser. No. 16/659,050, now U.S. Pat. No. 10,827,261, filed on Oct. 21, 2019. U.S. patent application Ser. No. 16/659,050 is a continuation of U.S. patent application Ser. No. 15/870,043, filed on Jan. 12, 2018, now U.S. Pat. No. 10,455,324. U.S. patent application Ser. No. 17/085,884, U.S. patent application Ser. No. 16/659,050, and U.S. patent application Ser. No. 15/870,043 are hereby incorporated by reference in their entireties Priority to U.S. patent application Ser. No. 17/085,884, U.S. patent application Ser. No. 16/659,050, and U.S. patent application Ser. No. 15/870,043 is hereby claimed.

FIELD OF THE DISCLOSURE

This disclosure relates generally to bone conduction and, more particularly, to apparatus and methods for bone conduction context detection.

BACKGROUND

When a subject speaks, vibrations from the subject's vocal cords induce vibrations in the bones of the subject's head. A bone conduction microphone records sounds as the user speaks based on vibrations detected by, for example, sensor(s) (e.g., vibration transducer(s) such as accelerometer(s)) coupled to the subject's scalp, jaw, cheeks, etc. In a bone conduction microphone, the transducer(s) convert the mechanical vibrations from the corresponding bones (e.g., cheekbones, jawbones) into electrical signals representative of the user's speech.

Bone conduction can also be used to transmit sound to the subject. Electrical signals can be converted into vibrations that are transferred to the bones of the subject's skull. The vibrations are transmitted to the subject's inner ear, thereby conveying sound to the subject while bypassing the subject's eardrum.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
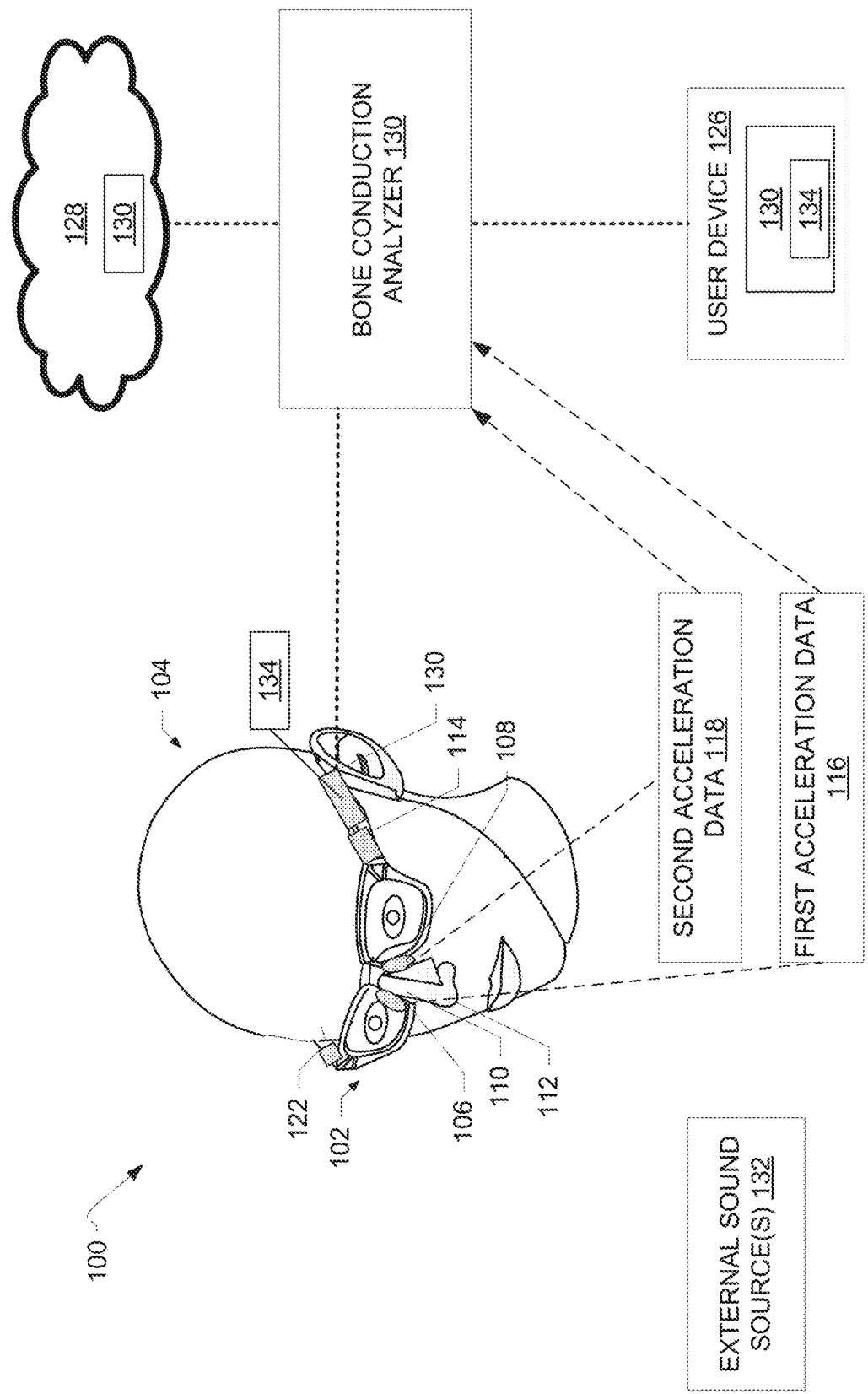
FIG. 1 illustrates an example system constructed in accordance with teachings disclosed herein and including a bone conduction device and a bone conduction analyzer for analyzing bone conduction data.

Bone conduction uses bone vibrations to transmit sound to a subject's inner ear (e.g., bypassing the eardrum) and/or to detect sounds generated while, for example, the subject is speaking. For example, one or more sensors, such as accelerometers, of a bone conduction microphone can be coupled to the subject's jaw, cheeks, temples, etc. and/or placed in contact with the subject's teeth. During a vocal activity such as speech, singing, etc., vibrations of the subject's vocal cords induce vibrations in the bones of the subject's head. The accelerometers detect the vibrations of the bones. The electrical signal data generated by the accelerometers can be converted into audio signal data (e.g., via signal processing) that is output by a speaker or other output device (e.g., converted to text and displayed). Bone conduction microphones can be used to detect speech with accuracy. Conventional air-conduction microphones typically pick up environmental background noises in addition to the subject's voice and, thus, may prove less accurate than bone conduction microphones.

Although vibration signal data collected via the sensor(s) of a bone conduction microphone typically contains less environmental noise data than air-conduction microphones, data collected via the sensor(s) of a bone conduction microphone may nonetheless include noise. For example, a subject may intentionally or unintentionally move his or her head while speaking. Such movements of the head can include, for example, rotation, tilting, etc. The motion of the subject's head can be detected by the accelerometers of the bone conduction microphone. Thus, the resulting signal data, because it is generated by accelerometers, can include a mixture of data indicative of speech (e.g., from the bone vibrations) and data indicative of motion (e.g., from the head movement). Also, in some examples, sounds from external sources, such as other people talking can be captured by the accelerometers as a result of sound waves having a frequency at which the accelerometers vibrate. Thus, data collected by the accelerometers of a bone conduction microphone can include data generated from subject activity (e.g., the wearer of the microphone speaking) and/or external source activity (e.g., another person speaking to the wearer of the microphone).

In examples disclosed herein, vibration data is derived from bone vibrations that are generated, for instance, as a subject performs a vocal activity such as speaking. In some examples, the vibrations are detected by one or more sensors disposed proximate to the subject's skin (e.g. facial skin). In some example disclosed herein, a subject wears a bone conduction microphone, which may be coupled to a wearable head-mounted device such as eyeglasses. In some examples, the bone conduction microphone includes at least one sensor disposed on a first (e.g., right) side of the subject's nose bridge and at least one sensor disposed on a second (e.g., left) side of the subject's nose bridge when the subject wears the device. The sensors can be coupled to, for example, the respective nose pads of the eyeglasses that rest on the sides of the subject's nose when the subject wears the eyeglasses. In some examples, the sensor disposed on the first side of the nose bridge is associated with a first bone conduction microphone and the sensor disposed on the second side of the nose bridge is associated with a second bone conduction microphone such that the user is wearing at least two bone conduction microphones.

In some examples, the sensors include accelerometers. As the subject speaks, the accelerometers respond to bone vibrations (e.g., nasal bone vibrations) caused by the speaking. Also, as the subject moves his or head, the same or other accelerometers measure the acceleration of the subject's movement(s). The accelerometers produce corresponding electrical signals that can be analyzed to distinguish speech data from motion data.

Example systems and methods disclosed herein analyze signal data collected by bone conduction microphone(s) (e.g., accelerometer data collected by accelerometers disposed proximate to a subject's nose) to differentiate between vocal activities performed by the subject (e.g., the subject's speaking) and head movement by the subject. Some examples identify sound (e.g., the subject's voice) data versus motion data based on phase differences between the signal data collected by the accelerometer disposed on the first side of the subject's nose and the signal data collected by the accelerometer disposed on the second side of the subject's nose. Some examples distinguish between sound data and motion data based on portions of the signal data from the accelerometers that are in-phase and portions of the signal data from the accelerometers that are out-of-phase. In some disclosed examples, the motion data (which can be considered noise relative to the sound data) can be reduced, substantially removed or even eliminated from the signal data by, for example, combining the signal data collected by each accelerometer. Thus, examples disclosed herein determine a context which data captured by the sensors of the bone conduction microphones originated, including the user speech and/or user motion.

Some disclosed examples analyze the data generated by the accelerometers of the bone conduction microphone(s) in substantially real-time (e.g., less than one second) via, for example a processor associated with (e.g., carried by) the wearable device (e.g., eyeglasses). Some disclosed examples analyze the bone conduction data via a processor of a user device that is different from the wearable device that collects the data. For instance, the processor of a smartphone and/or other wearable such as a watch or the like may perform the data analysis. Other examples export the data to one or more cloud-based device(s) such as server(s), processor(s), and/or virtual machine(s) to perform the analysis.

In examples disclosed herein, bone conduction data can be efficiently filtered to remove noise corresponding to motion of the subject wearing the microphone based on analysis of the phase differences between the signal data collected from each side of the subject's head. The filtered data can be used to more accurately generate audio data for output via one or more speakers and/or to more accurately generate other type(s) of output(s). Examples disclosed herein provide for efficient noise cancellation in data generated by the bone conduction microphone without requiring dedicated signal filters and without consuming significant resources (e.g., power, processing cycles), etc. because such noise cancellation can be achieved by simply adding or subtracting the signals to cancel in-phase or out-of-phase portions of the data (which may correspond to motion data). In examples where a subject may be moving while speaking and/or listening, such as when the subject is giving a presentation, riding a bike alongside another rider, etc., the motion data can be extracted from the speech data to reduce distortion and/or improve clarity of the corresponding audio data output by the bone conduction microphone.

Some disclosed examples compare phase and magnitude between the signal data generated by the accelerometers to determine if the sound data (e.g., voice data) originates from the subject or from an external source. The determination of the source of the sound data (e.g., data representative of speech) can be used, for example to authenticate (e.g., identify) the wearer of the wearable device to enable the user to access, for example, one or more user applications installed on a wearable or non-wearable user device. In some such examples, the magnitude of the signal data is compared to determine a direction from which the external sound originated relative to the subject (e.g., to the right or left of the subject, in front of the subject, behind the subject, etc.). The identified direction can be used for many applications. For example, the direction information can be provided to, for instance, a visually impaired subject via one or more alerts or notifications that are presented via the wearable device including the bone conduction microphone or another device in proximity to the subject (e.g., a tactile transducer) to assist the subject. Thus, examples disclosed herein provide contextual information about the sound data as originating from the subject or external sound source(s).

Although examples disclosed herein are discussed in the context of sound data such as speech, teachings disclosed herein can be utilized in other applications such as identifying user breathing rate based on breathing data collected via the sensors of the wearable device. As such, the discussion of sound (e.g., speech) data and/or motion data is for illustrative purposes only and does not limit this disclosure to applications involving sound data such as speech.

FIG. 1 illustrates an example system 100 constructed in accordance with teachings of this disclosure for identifying sound (e.g., voice) data with respect to a subject or user. The term "user" and "subject" are used interchangeably herein and both refer to a biological creature such as a human being. The example system 100 includes a wearable device 102 to be worn by the user 104. In the example of FIG. 1, the wearable device 102 includes eyeglasses worn by the user 104. However, the wearable device 102 can additionally or alternatively include other wearables, such as a mask, a nasal strip, a hat, a headband, an eye patch, etc.

The wearable device 102 of the illustrated example includes at least a first sensor 106 and a second sensor 108. In the example of FIG. 1, the first and second sensors 106, 108 are accelerometers such as single axis accelerometers, dual axis accelerometers, etc. In the example of FIG. 1, the sensors 106, 108 are coupled to the wearable device 102 such that, when the user 104 wears the wearable device 102, the first sensor 106 is disposed proximate to a first (e.g., right) side of a bridge 110 of a nose 112 of the user 104 and the second sensor 108 is disposed proximate to a second (e.g., left) side of the user's nasal bridge 110. The sensors 106, 108 are positioned so at least a portion of the respective sensors 106, 108 is touching the skin of the user 104 (e.g., the skin of the user's nose 112). For example, the sensors 106, 108 can be coupled to nose pads of the wearable device 102 (e.g., eyeglasses) to enable the sensors 106, 108 to rest on the user's nose 112 when the user 104 is wearing the wearable device 102.

As the user 104 wears the device 102, bone vibrations representative of sound can be detected. For example, when the user 104 performs a vocal activity such as speaking, singing, screaming, etc., the sensors 106, 108 detect bone vibrations generated as a result of the vocal activity (e.g., bone vibrations detected via corresponding motion of the user's skin). In some examples, the sensors 106, 108 detect vibrations of the nasal bones proximate to the nasal bridge 110. In particular, the sensors or accelerometers 106, 108 generate electrical signal data based on the vibrations of the nasal bridge 110 (e.g., during the vocal activity or resulting from externally generated sounds). In some examples, an orientation of the first sensor 106 and/or an orientation of the second sensor 108 relative to the user's nose 112 are adjusted to enable the sensors 106, 108 to detect equal or substantially equal vibration amplitudes as the user is speaking. For example, the sensor(s) 106, 108 can be positioned substantially straight relative to the respective sides of the user's nose 112 or at a same angle (e.g., slanted) relative to the sides of the user's nose 112. The exact positioning is application dependent based on such features as the geometry of the user's nose, which may or may not be symmetric.

In some instances, the sensors 106, 108 collect data caused by external sound source(s) 132 (e.g., based on sound waves having a frequency at which the accelerometers vibrate). The external sound source(s) 132 can include, for example, individual(s) speaking to the user 104, a media-playing device (e.g., the user device 126, another device), environmental noise (e.g., car noise, a passing train, airplane noise, crowd noise, etc.).

The sensors 106, 108 may measure bone vibrations and/or collect external sound data continuously and/or for specific period(s) of time. For example, the sensors 106, 108 and/or the device 102 may collect data whenever the user 104 is wearing the wearable device 102, for a specific duration (e.g., always on when the user is wearing the device 102), etc. In other examples, the sensors 106, 108 additionally or alternatively measure bone vibrations at other portions of the user's body. For example, the sensor(s) 106, 108 can be disposed proximate to the user's cheeks, the user's temples, the user's forehead, the user's neck, the user's ears, and/or proximate other body regions to measure vibrations of the corresponding bones in those regions. The wearable device 102 can include additional sensors 106, 108 than illustrated in FIG. 1.

In the example of FIG. 1, the first sensor 106 and the second sensor 108 are in communication with at least one speaker 114 carried by the wearable device 102. In use, the speaker 114 can be used to output audio data based on the electrical signal data generated by the sensors 106, 108 from the detected bone vibrations. The speaker 114 can be an acoustic audio speaker that outputs audio into free space based on bone vibrations generated when the user speaks. In some examples, the speaker 114 is a bone conduction speaker that provides audio to the user by causing bone vibrations in the user in response to sound wave(s) generated by external source(s) and detected by the sensor(s) 106, 108, thereby passing the user's eardrum. In some examples, one or both types of speakers are present. In the illustrated example of FIG. 1, the example wearable device 102 includes at least one speaker. Although in the example of FIG. 1, the speaker 114 is shown positioned adjacent a temple of the user, the speaker 114 can be disposed at a different location of the wearable device 102 than that illustrated in FIG. 1. For instance, the speaker 114 can be disposed proximate to the nose pads of the example eyeglasses of FIG. 1. In examples where the speaker 114 is a bone conduction speaker, the speaker 114 can be coupled to the wearable device so as to rest proximate to one or more of the user's ears. The example wearable device 102 can include additional speakers (e.g., bone conduction and/or acoustic audio speakers). For example, the first sensor 106 can supply data to a first speaker and the second sensor 108 can supply data to a second speaker.

The example system 100 of FIG. 1 includes one or more bone conduction analyzers 130 to process the first acceleration data 116 (e.g., first bone vibration information) generated by the first sensor 106 and the second acceleration data 118 (e.g., second bone vibration information) generated by the second sensor 108, and/or to generate one or more outputs based on the acceleration data 116, 118 (e.g., for output via the speaker(s) 114). For example, as illustrated in FIG. 1, the bone conduction analyzer 130 is carried by (e.g., mounted on) the wearable device 102. In the example of FIG. 1, the bone conduction analyzer 130 is in communication with (e.g., directly or indirectly communicatively coupled to) the first sensor 106, the second sensor 108, and the speaker(s) 114. The wearable device 102 of FIG. 1 includes a battery 122 to provide power to the bone conduction analyzer 130 and/or other components of the wearable device 102.

In other examples, the bone conduction analyzer 130 is separate from the wearable device 102. For example, the sensor(s) 106, 108 can wirelessly transmit acceleration data 116, 118 to the bone conduction analyzer 130 located in a user device 126 such as a smartphone or another wearable (e.g., a smart watch). In other examples, the sensor(s) 106, 108 can transmit the acceleration data 116, 118 to a cloud-based bone conduction analyzer 130 (e.g., implemented by one or more server(s), processor(s), and/or virtual machine(s)). The dotted lines extending from the bone conduction analyzer 130 in FIG. 1 are intended to show the bone conduction analyzer 130 can be located in any of these locations and/or distributed among two or more of these locations (e.g., on the wearable 102, in the cloud 128, and/or in a wearable or non-wearable user device 126). The sensor(s) 106, 108 of the wearable device 102 can wirelessly communicate with the bone conduction analyzer 130 via WiFi, Bluetooth, and/or other wireless communications protocols supported by the sensor(s) and the device(s). Alternatively or additionally, the communication can be a wired connection.

In some instances, the user 104 may move his or her head while listening and/or performing a vocal activity such as speaking. For example, the user 104 may rotate or tilt his or head to the right, to the left, or between the right and the left directions. In the example system 100, the sensors 106, 108 collect acceleration data 116, 118 as the user 104 performs the movement. In some examples, the acceleration data 116, 118 includes sound data indicative of vibrations due to sound (e.g., spoken and/or heard by the user) and motion data as a result of the movement by and/or of the user 104 as detected by the sensors 106, 108 (e.g., changes in acceleration due to the head motion and/or due to external forces such a bumps while riding a bicycle). In some examples, the bone conduction analyzer 130 processes (e.g., combines) the acceleration data 116, 118 to remove or substantially remove the motion data (e.g., which can be considered noise relative to the sound data).

In some instances, the sensors 106, 108 collect data caused by the external sound source(s) 132 (e.g., individual(s) speaking to the user 104, media-playing device(s), etc.). In the example of FIG. 1, the bone conduction analyzer 130 processes the acceleration data 116, 118 to identify whether the sound data (e.g., voice data) originated from the user 104 or one or more external sound source(s) 132. The bone conduction analyzer 130 additionally or alternatively determines a direction in which sound data from the external sound source(s) 132 originated relative to the user 104 (e.g., to the right of the user, to the left of the user, in front of the user, behind the user, and/or a combination of such directions). In some examples, based on the identification of the origination of the sound data, the example bone conduction analyzer 130 authenticates the user 104 as the source of the sound data (e.g., if the sound originates with the user speaking). Based on the authentication, the user 104 may be permitted to perform one or more activities via user application(s) executed by the wearable device 102 and/or the other user device 126, such as making a telephone call, accessing media such as music to be played via the user device(s) 102, 126, etc.

In some other examples, the sensors 106, 108 collect data such as breathing data as the user breathes in and out while wearing the wearable device 102. Thus, the discussion herein of acceleration data 116, 118 generated in response to sound data (e.g., speech by the user) is not limited to sound data but can include other types of data detected by the sensors 106, 108, such as vibrations due to breathing.

In some examples, the bone conduction analyzer 130 receives and processes the acceleration data 116, 118 in substantially real-time (e.g., near the time the data is collected such as within one second or within 500 ms). In other examples, the bone conduction analyzer 130 receives the acceleration data 116, 118 at a later time (e.g., periodically and/or aperiodically based on one or more settings but sometime after the sound has occurred (e.g., seconds, minutes, hours, days, etc. later)).

The example bone conduction analyzer 130 of FIG. 1 analyzes the acceleration data 116, 118 from the sensors 106, 108 to distinguish between data indicative of bone vibrations due to sound (e.g., voice data) and data due to motion of the user's head. For example, the bone conduction analyzer 130 compares phases of the acceleration data 116 collected by the first sensor 106 with the phases of corresponding portions of the acceleration data 118 collected by the second sensor 108 to determine whether the corresponding portions are in-phase or out-of-phase.

In the illustrated example, the first sensor 106 detects vibrations at the right side of the user's nasal bridge 110 along at least one axis (e.g., a Z-axis) and the second sensor 108 detects vibrations at the left side of the user's nasal bridge 110 along the same axes (e.g. the Z-axis). The respective signal data generated by the sensors 106, 108 can exhibit different phase characteristics based on whether the data corresponds to sound or motion. For example, when the user rotates his or her head, the sensors 106, 108 both detect motion the same direction (e.g., in the direction the user is rotating his head, such as to the right or the left). Thus, the signal data generated by the sensors 106, 108 in response to user motion may be in-phase. However, when the user speaks, the first sensor 106 may detect bone vibrations (e.g., nasal bone vibrations) in a first direction (e.g., along the Z-axis in the positive direction) and the second sensor 108 may detect bone vibrations in a second direction (e.g., along the Z-axis in the negative direction) due to the placement of the sensors on opposite sides of the user's nasal bridge. As a result, acceleration data generated by the respective sensors 106, 108 during, for example, speech may be out-of-phase. The bone conduction analyzer 130 can remove the portions of the acceleration data 116, 118 corresponding to motion data by combining the acceleration data 116, 118 (e.g., adding or subtracting based on phase differences). In some examples, the bone conduction analyzer 130 removes the portions of the acceleration data 116, 118 corresponding to sound data by combining the acceleration data 116, 118 (e.g., adding or subtracting based on phase differences).

In some examples, the bone conduction analyzer 130 identifies differences in phase and magnitude between data collected by the first sensor 106 and data collected by the second sensor 108 to determine whether the sound data originated from the user 104 (e.g., the wearer of the device 102) or from an external sound source 132. In some examples, the bone conduction analyzer 130 analyzes the sensor data using particular (e.g., predefined) rules that distinguish between sound originating from the user and sound originating from an external source. For example, the rule(s) can indicate that if the magnitude of the data collected by the first sensor 106 is greater than the magnitude of the data collected by the second sensor 108, the sound data originated from an external sound source 132 is disposed proximate to the side of the user on which the first sensor 106 is disposed (e.g., the right size).

In some examples, the bone conduction analyzer 130 generates one or more outputs based on the identification of sound data, the identification of the motion data, and/or the determination of the direction of origination of the sound data (e.g., from the user or from an external sound source 132 in direction x relative to the user). The outputs can include, for example, noise-cancelled signal data (e.g., signal data in which the motion data has been removed or substantially removed). The noise-cancelled signal data can be provided to, for example, the speaker(s) 114 of the wearable device 102 to improve a quality of the sound output by the speaker(s) 114 (e.g., based on the bone vibration data) by removing the noise caused by user movement, such as when the user 104 is wearing the wearable device 102 while playing a sport.

In some examples, the outputs of the bone conduction analyzer 130 can include user authorization instruction(s) provided to one or more user applications 134 installed on, for example, the wearable device 102 and/or the user device 126 based on a user authentication process. The user authorization instruction(s) can be generated by the bone conduction analyzer 130 based on the determination that the sound data originated from the user 104 (e.g., the wearer of the wearable device 102) rather than external sound source(s) 132. In other examples, the user authorization instruction(s) may deny access by the user 104 (or another user) to the user application(s) 134 based on the determination that the sound data originated from an external sound source (e.g., the user was not authenticated by the detected voice signal). The user application(s) 134 installed on the wearable device 102 and/or on the user device 126 can include, for example, a telephone application, a media-presentation application (e.g., music playing application), an application to control one or more other devices (e.g., to unlock a door in a room in which the user 104 is located), etc. Thus, the determination of whether the sound data originated from the user 104 and/or external sound source(s) 132 can be used to control secure access to user application(s) 134 installed on the device(s) 102, 126, and/or other devices.

Additionally or alternatively, the generation of the user authentication instruction(s) can be based on the identification of sound (e.g., voice) data after being filtered of the motion data. In such examples, the bone conduction analyzer 130 ensures user access to and/or operation of the user application(s) 134 is based on the detection of voice data and not, for instance, based on motion data collected incidentally while the user 104 is wearing the wearable device 102.

In other examples, the system 100 may facilitate two factor authentication. For example, the bone conduction analyzer may generate the user authentication instructions for one or more user application(s) 134 and/or device operations based on both the sound data and the motion data. For example, user authentication may only occur when the user speaks a password while moving his or her head in a predefined manner (e.g., while turning his or her head to the left).

In some examples, the generation of the user authorization instruction(s) is based on identification of one or more features of the sound data. For example, the bone conduction analyzer 130 can identify features of the voice making the sound based on known voice features for one or more users (e.g., known speech characteristics, tones, known voice data magnitude thresholds defined for the user 104 and/or other users, etc.). In such examples, the bone conduction analyzer 130 performs a voice authentication analysis of the sound data to verify the user 104 and to permit or deny access to the user application(s) 134 via the user authorization instruction(s).

In some examples, the outputs of the bone conduction analyzer 130 can include alerts or notifications to the user 104 as to the direction of sound originating from an external sound source 132 as determined by the bone conduction analyzer 130. The alerts or notifications can be presented via the wearable device 102 (e.g., in the form of vibrations, sounds, visual signals, etc.) and/or the user device 126 (e.g., in the form of vibrations, sounds, visual and/or audio alerts). In some such examples, the alerts and/or notifications can assist a wearer of the wearable device 102 (e.g., who may be visually impaired) by providing information to the wearer about the source of external sound(s) (e.g., a person speaking to the user 104).

Figure 2:
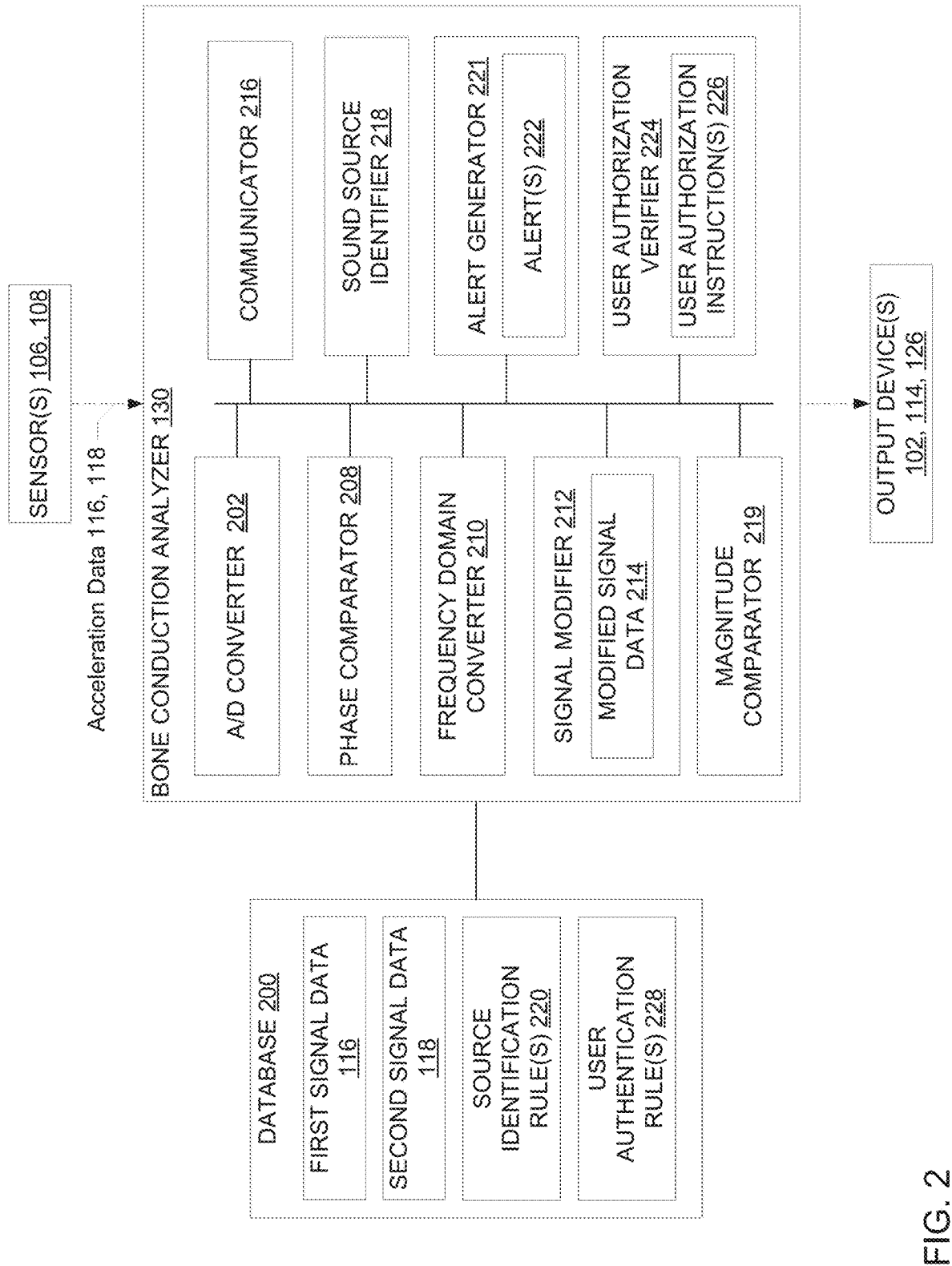
FIG. 2 is a block diagram of an example implementation of the bone conduction analyzer of FIG. 1.

FIG. 2 is a block diagram of an example implementation of the bone conduction analyzer 130 of FIG. 1. As mentioned above, the example bone conduction analyzer 130 is constructed to distinguish sound (e.g., voice) data from motion data generated due to user movement (e.g., movement of the user's head). The sound data may be generated externally of the user or may be generated by vocal activity by the user (e.g., speech by the user 104 of FIG. 1). Therefore, the example bone conduction analyzer 130 is constructed to identify a source of the sound data as originating from the user 104 or originating from an external sound source (e.g., the external sound source 132 of FIG. 1).

The example bone conduction analyzer 130 of FIG. 2 has access to a database 200. In this example, the database 200 is stored in a local memory device carried by the wearable device 102. In other examples, the database 200 is located external to the wearable device 102 in a location accessible to the analyzer 130. In some examples, the acceleration signal data 116, 118 generated by the sensors 106, 108 is transmitted to the bone conduction analyzer 130 and then delivered to the database 200. Thus, in the illustrated example, the database 200 provides means for storing first signal data 116 (e.g., acceleration data or first bone vibration information) generated by the first sensor 106 and second signal data 118 (e.g., acceleration data or second bone vibration information) generated by the second sensor 108.

The example bone conduction analyzer 130 of FIG. 2 includes an analog-to-digital (A/D) converter 202. In the illustrated example, the A/D converter 202 provides means for sampling the raw analog accelerometer signal data 116, 118 at a particular sampling rate and converting the analog signal data to digital signal data for analysis by the example bone conduction analyzer 130. The example database 200 may store the signal data 116, 118 before and/or after the data is processed by the A/D converter 202.

The example bone conduction analyzer 130 of FIG. 2 includes a phase comparator 208. In the illustrated example, the phase comparator 208 provides means for identifying phase differences in the signal data 116, 118. In the example of FIG. 2, the phase differences identified by the phase comparator 208 can be indicative of signal data including a mixture of sound data and motion data. The presence of motion data in the signal data 116, 118 can interfere with, for example, the quality of audio output by the speaker(s) 114.

For example, the phase comparator 208 of this example aligns signal data 116, 118 in the time domain over the time period for which the data was collected or one or more segments thereof. For example, the phase comparator 208 aligns a first portion of the first acceleration data 116 beginning at time $T_1$ and ending at time $T_2$ with a second portion of the second acceleration data 118 beginning at time $T_1$ and ending at time $T_2$. The phase comparator 208 analyzes the aligned signal data 116, 118 to identify any phase differences between the signal data 116, 118. For example, the phase comparator 208 compares the phase of, for example, the first portion of the first signal data 116 collected over a first time period with the phase of the second portion of the second signal data 118 collected over the same time period. The phase comparator 208 determines if the first and second portions of the signal data 116, 118 are in-phase or out-of-phase.

In the example of FIG. 2, if the phase comparator 208 determines that the aligned signal data 116, 118 includes in-phase portions and out-of-phase portions, then the signal data 116, 118 may include a mixture of data indicative of user speech and data indicative of user motion. For example, the in-phase portions can represent sound data and the out-of-phase portions can represent motion data based on conventions assigned to the data collected by the sensors 106, 108 with respect to the directions in which the sensors 106, 108 detect the bone vibrations and/or the user motion. For examples, sensors 106, 108 can be configured or wired as mirror images of one another such that sound data generated by the sensors 106, 108 is represented as being in-phase.

The identification of phase differences between the signal data 116, 118 by the phase comparator 208 can facilitate removal of, for example, the motion data from the signal data 116, 118 by the bone conduction analyzer 130. For example, as discussed herein, based on the detection of out-of-phase portions in the signal data, which can represent motion data, the bone conduction analyzer 130 removes or filters the motion data from the signal data. The filtered signal data can be used to produce, for example, an output (e.g., audio output) that does not include signal interference from user movement(s), such as rotation of the user's head while speaking and/or listening.

The example bone conduction analyzer 130 of FIG. 2 includes signal modifier 212. In the illustrated example, the signal modifier 212 provides means for separating sound data and motion data in the signal data 116, 118. As discussed above, in some examples, the phase identifier 208 determines that the signal data 116, 118 includes sound data (e.g., based on the portions of the time-aligned signal data 116, 118 that are in-phase) and motion data (e.g., based on the portions of the time-aligned signal data 116, 118 that are out-of-phase). In some such examples, the example signal modifier 212 of FIG. 2 modifies the signal data 116, 118 to remove or substantially remove the motion data from the signal data, which may represent noise as compared to the sound (e.g., voice) data.

For instance, in the example of FIG. 2, the signal modifier 212 combines the time-aligned first signal data 116 and second signal data 118 to generate modified (e.g., filtered) signal data 214. As noted above, the in-phase portions of the signal data 116, 118 can correspond to sound data and the out-of-phase portions of the signal data 116, 118 can correspond to the motion data. In such examples, the signal modifier 212 can sum the data 116, 118 to cancel the motion data. Thus, in some examples, the signal modifier 212 is an adder. Summing the in-phase portions of the signal data 116, 118 increases the amplitude of the in-phase portions. Summing the out-of-phase portions of the signal data 116, 118 results in cancellation or substantial cancellation of the out-of-phase portions. Thus, summing the signal data 116, 118 removes or substantially reduces the motion data (e.g., noise data as compared to the sound data) from the signal data 116, 118. The resulting modified signal data 214 includes sound data without or substantially without motion data. Thus, the example signal modifier 212 of FIG. 2 uses the phase differences identified by the phase comparator 208 to cancel or substantially cancel the motion data (e.g., noise) from the signal data. Thus, by summing the signal data 16, 118 to substantially cancel noise (e.g., motion data) from the signal data, the example signal modifier 212 provides alternative means for filtering the data to remove noise as compared to, for example, filtering based on frequency bands.

In other examples, the signal modifier 212 may subtract the signal data to generate the modified signal data 214. For example, in instances in which sound data is represented by out-of-phase signal data 116, 118, the signal modifier 212 may subtract the signal data 116, 118 to increase an amplitude of the sound data. In instances in which motion data is represented by out-of-phase signal data 116, 118, the signal modifier 212 may subtract the signal data 116, 118 to increase an amplitude of the motion data (e.g., to analyze the motion components of the data).

In the example of FIG. 2, whether the signal modifier 212 sums the signal data 116, 118 to obtain sound data without or substantially without motion data or whether the signal modifier 212 takes the difference of the signal data 116, 118 to obtain sound data without or substantially without motion data is based on the wiring of the sensors. As discussed above, the sensors 106, 108 can be configured or wired as mirror images of one another such that sound data generated by the sensors 106, 108 is represented as in-phase and motion data is represented as out-of-phase. In such examples, the signal modifier 212 sums the data to obtain the sound data without motion data and takes the difference of the data to obtain motion data without the sound data. In other examples, the sensors 106, 108 can be configured such that sound data is represented as out-of-phase and the motion data is represented as in-phase. In such examples, the signal modifier 212 takes the difference of the data to obtain the sound data without sound data and sums the data to obtain motion data without the sound data.

In some examples, the bone conduction analyzer 130 of FIG. 2 does not include the A/D converter 202. In such examples, the noise cancellation performed by the signal modifier 212 can be based on the raw data generated by the sensors 106, 108. For example, the signal modifier 212 can sum the raw analog signal data. In examples where one or more portions of the signal analysis is performed by the bone conduction analyzer 130 on-board the wearable device 102 and one or more portions of the signal analysis is performed by the bone conduction analyzer 130 at a device other than the wearable device 102 (e.g., the user device 126), the signal modifier 212 of the bone conduction analyzer 130 on-board the wearable device 102 may remove, for example, data indicative of user motion, from the analog data. The bone conduction analyzer 130 of the wearable device 102 can transmit the filtered analog data for further processing off-board the wearable device 102.

In some examples, the bone conduction analyzer 130 of FIG. 2 includes a frequency domain converter 210 to convert the signal data from the time domain to the frequency domain. For example, the first portion of the first signal data 116 may include several frequency components, some of which represent sound and some of which represent user motion. The second portion of the second signal data 118 may similarly include such multiple frequency components. To analyze these components, the frequency domain converter 210 of the example bone conduction analyzer 130 may convert the first and second portions of the signal data 116, 118 from the time domain to the frequency domain via, for example, a Fast Fourier Transform (FFT). The frequency components of the first and second portions can then be compared in the frequency domain to identify frequencies that are out of phase between the first and second portions of the signal data 116, 118. The out-of-phase frequency components can then be removed by the signal modifier 212 from either the first portion of the second portion to thereby filter the noise (e.g., motion data) from the first or second portions of whatever signal data 116, 118 is to be used for outputting the audio.

The example bone conduction analyzer 130 of FIG. 2 includes a communicator 216. In the illustrated example, the communicator 216 of FIG. 2 includes means for communicating with one or more output devices 102, 114, 126. For example, the signal modifier 212 can instruct the communicator 216 to transmit the modified signal data 214 for output (e.g., as an audio signal) by the speaker(s) 114. In some examples, the communicator 216 transmits the modified signal data 214 to the output device(s) in substantially real-time as the modified signal data 214 is generated by the signal modifier 212. In other examples, the communicator 216 transmits the modified signal data 214 at periodic intervals based on particular (e.g., predefined) settings.

In some examples, the bone conductor analyzer 130 receives sensor data from one or more other sensors of the wearable device 102 and/or of another wearable or non-wearable device (e.g., the user device 126). The additional sensor data can include, for example, heart rate data or motion data from accelerometers of another device (e.g., a smartwatch). In some such examples, the communicator 216 can provide the provide the modified signal data 214 in connection with the data received from other sensor(s) and/or device(s) to provide additional information about the user's activities (e.g., playing a sport). For example, modified signal data 214 including motion data can be used in connection with motion data received from a smartwatch to track user activities as part of a health plan for the user.

As discussed above, in some examples, the sensors 106, 108 generate data due to sound from external sound source(s) 132, such as individual(s) speaking in proximity to the wearer of the wearable device 102 (e.g., the user 104), environmental noises, media-playing devices, etc. For example, the signal data 116, 118 can include data from external sound(s) having frequency(ies) that induce response(s) by the sensor(s) 106, 108 (e.g., frequencies that cause the accelerometer(s) 106, 108 to vibrate and, thus, collect data).

The example bone conduction analyzer 130 of FIG. 2 includes a sound source identifier 218. In the illustrated example, the sound source identifier 218 provides means for identifying whether sound data in the signal data 116, 118 originated from the wearer of the wearable device 102 or from external sound source(s) 132 based on analysis of the signal data in view of one or more predefined source identification rule(s) 220 stored in the database 200. In some examples, the sound source identifier 218 of FIG. 2 analyzes phase and magnitude differences between the respective signal data 116, 118 collected by the sensors 106, 108 to determine whether the sound data originated from the user 104 or from an external sound source 132. In some examples, the sound source identifier 218 determines direction(s) in which the external sound(s) originated relative to the user 104 (e.g., in front of the user, to the left of the user) based on phase and/or magnitude characteristics of the signal data 116, 118.

For example, the frequency domain converter 210 of FIG. 2 can convert the time domain signal data 116, 118 to the frequency domain (e.g., via Fast Fourier Transform). The phase comparator 208 can analyze the signal data 116, 118 in the frequency domain to identify frequencies that are out of phase between the signal data 116, 118. In some other examples, the phase comparator 208 identifies phase differences between the signal data in the time domain.

The example bone conduction analyzer 130 of FIG. 2 can include a magnitude comparator 219. The example magnitude comparator 219 of FIG. 2 provides means for identifying differences in magnitude between portion(s) of the first signal data 116 and portions of the second signal data 118. In some examples, the magnitude comparator 219 of FIG. 2 compares the magnitude of the signal data in the frequency domain. In other examples, the magnitude comparator 219 of FIG. 2 compares the magnitude of the signal data in the time domain.

In the example of FIG. 2, the sound source identifier 218 applies one or more source identification rule(s) 220 to identify the source of the sound data based on the phase differences between the signal data 116, 118 identified by the phase comparator 208 and/or the magnitude differences between the signal data 116, 118 identified by the magnitude comparator 219. In some examples, the sound source identifier 218 uses the source identification rule(s) 220 to determine the direction of an external sound source relative to the user. The source identification rule(s) 220 can be defined by user input(s) received by the bone conduction analyzer 130.

For example, the source identification rule(s) 220 can include a rule that sound (e.g., voice) data generated by the user 104 corresponds to portions of the signal data 116, 117 that are in-phase and have substantially equal magnitude (e.g., within threshold range). The source identification rule(s) 220 can include a rule that sound data generated by the external sound source(s) 132 corresponds to out-of-phase portions of the signal data 116, 118. Another example rule 220 can indicate that portions of the signal data 116, 118 that are out-of-phase and that have substantially unequal magnitudes between the portions represent external sound(s) generated by an external sound source 132 that is disposed proximate to the right of the user 104 or to the left of the user 104. Another example rule 220 can indicate that if the signal data generated by the first sensor 106 has larger magnitude than the signal data generated by the second sensor 108, then the external sound source 132 is disposed to the right of the user 104. Another example rule 220 can indicate that if the signal data generated by the second sensor 108 has larger magnitude than the signal data generated by the first sensor 106, then the external sound source is disposed 132 to the left of the user 104. Another example rule 220 can indicate that sound data generated by an external sound source 132 that is disposed substantially in front of the user 104 (e.g. substantially in front of the face of the user 104) includes signal data generated by the respective sensors 106, 108 that is in-phase and has substantially equal magnitudes, but the magnitudes are smaller than the signal data generated by the sensors 106, 108 when the user 104 is the source of the sound data (e.g., when the user is speaking).

The source identification rule(s) 220 can be based on, for example, known data collected from a plurality of users, including, in some examples, the user 104. In some examples calibration data can be obtained from the user 104 wearing the wearable device 102 to obtain average magnitudes of sound data generated by the user (e.g., when the user is speaking). The calibration data can be used to define thresholds or ranges to enable the sound source identifier 218 to distinguish between sound generated by the user and sound data generated by the external sound source(s). Such user-specific thresholds or ranges may be used by the sound source identifier 218 in examples where the external sound source 132 is disposed substantially in front of the user. As mentioned above, signal data for sound data generated by the user 104 and signal data for sound data generated by the external sound source when the external sound source is disposed in front of the user may both include portions that are substantially in-phase. In such examples, the user-specific sound data thresholds can be used by the sound source identifier 218 to determine if the sound data originated from the user or the external sound source.

In some examples, the signal data collected by the sensors 106, 108 when the external sound source is disposed in-front of the user and the signal data collected by the sensors 106, 108 when the external sound source is disposed behind the user (behind the user's head) are both characterized by in-phase portions having substantially equal magnitudes. In such examples, the sound source identifier 218 may determine that the external sound source 132 is located in front of the user 104 or behind the user 104 based on directional information (e.g., coordinates) obtained by two-axis accelerometers 106, 108.

The example bone conduction analyzer 130 of FIG. 2 includes an alert generator 221. In the illustrated example, the alert generator 221 provides means for determining whether one or more alerts 222 should be generated and means for activating one or more outputs devices to generate alert(s) 222. For example, based on the determination of the direction in which the external sound source originated relative to the user 104 by the sound source identifier 218, the alert generator 221 determines the alert(s) 222 to be generated by the bone conduction analyzer 130 and activates the output device(s) (e.g., the wearable device 102, the wearable or non-wearable user device 126, another device in communication with the cloud-based device 128) to generate the alert(s) 222. The alert(s) 222 can include audio, visual, and/or tactile alert(s) informing the user 104 of the direction in which the external sound originated relative to the user 104. For example, the alert generator 221 may determine that an audio alert including the word "left" and/or a tactile alert including vibration of a portion of the wearable device 102 proximate to the left side of the user's head should be output if the sound source identifier 218 determines that an external sound originated from an external sound source disposed to the left of the user 104. In some examples, the format and/or content of the alert(s) 222 are customized based on user setting(s), the type of output device (e.g., whether the output device includes a display screen), and/or user characteristic(s) (e.g., visual impairments).

The example bone conduction analyzer 130 of FIG. 2 includes a user authorization verifier 224. In the illustrated example, the user authorization verifier 224 provides means for authenticating the user based on analysis of the sound (e.g., voice) data by the phase comparator 208 and/or the sound source identifier 218. The example user authorization verifier 224 of FIG. 2 provides means for generating one or more user authorization instructions 226 based on the authentication of the user. The user authorization instruction(s) 226 can include, for example, instruction(s) indicating that the user 104 is authorized to access one or more user applications 134 of the wearable device 102 and/or the user device 126 (e.g., a media player, a data sharing application, etc.).

The example user authorization verifier 224 of FIG. 2 generates the user authorization instruction(s) 226 based on one or more user authentication rule(s) 228. The user authorization rule(s) 228 can be defined by one or more user inputs and can include conditions to be satisfied for authenticating the user 104 based on the signal data generated by the sensors 106, 108. For example, the user authentication rule(s) 228 can includes an instruction that that the sound source identifier 218 determine that the sound data originate from the user 104 rather than from an external sound source 132 to authenticate the user. As another example, the user authentication rule(s) 228 can include an instruction that the phase comparator 208 identify signal data including sound data without motion data or a combination of sound data and motion data within a period of time to ensure that user access is not unintentionally tripped by only motion data collected incidentally while the user is wearing the wearable device 102. The user authentication rule(s) 228 can include amplitude thresholds associated with, for example, known characteristics of sound data generated by the user. The user authentication rule(s) 228 can be stored in the example database 200 of FIG. 2. In the example of FIG. 2, the communicator 216 transmits the user authorization instruction(s) 226 generated by the user authorization verifier 224 based on the rule(s) 228 to the output device(s) (e.g., the wearable device 102, the wearable or non-wearable device 126).

As mentioned above, in some examples, the bone conduction analyzer 130 receives sensor data from other sensor(s) and/or other device(s), such a heart data, motion data, etc. In some such examples, the alert generator 221 and/or the user authorization verifier 224 may generate the alert(s) 222 and/or the instruction(s) 226 based on the sensor data in addition to the determination of the origination of the sound data by sound source identifier 218. For example, the user authorization verifier 224 may generate user authorization instruction(s) 226 based on the determination that the sound data originated from the user and motion data indicating that the user raised his arm.

While an example manner of implementing the example bone conduction analyzer 130 is illustrated in FIGS. 1 and 2, one or more of the elements, processes and/or devices illustrated in FIGS. 1 and 2 may be combined, divided, re-arranged, omitted, eliminated and/or implemented in any other way. Further, the example database 200, the example A/D converter 202, the example phase comparator 208, the example frequency domain converter 210, the example signal modifier 212, the example communicator 216, the example sound source identifier 218, the magnitude comparator 219, the example alert generator 221, the example user authorization verifier 224 and/or, more generally, the example bone conduction analyzer 130 of FIGS. 1 and 2 may be implemented by hardware, software, firmware and/or any combination of hardware, software and/or firmware. Thus, for example, any of the example database 200, the example A/D converter 202, the example phase comparator 208, the example frequency domain converter 210, the example signal modifier 212, the example communicator 216, the example sound source identifier 218, the magnitude comparator 219, the example alert generator 221, the example user authorization verifier 224 and/or, more generally, the example bone conduction analyzer 130 of FIGS. 1 and 2 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example database 200, the example A/D converter 202, the example phase comparator 208, the example frequency domain converter 210, the example signal modifier 212, the example communicator 216, the example sound source identifier 218, the example magnitude comparator 219, the example alert generator 221, the example user authorization verifier 224 and/or, more generally, the example bone conduction analyzer 130 of FIGS. 1 and 2 is/are hereby expressly defined to include a non-transitory computer readable storage device or storage disk such as a memory, a digital versatile disk (DVD), a compact disk (CD), a Blu-ray disk, etc. including the software and/or firmware. Further still, the example bone conduction analyzer 130 of FIGS. 1 and 2 may include one or more elements, processes and/or devices in addition to, or instead of, those illustrated in FIGS. 1 and 2, and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Figure 3:
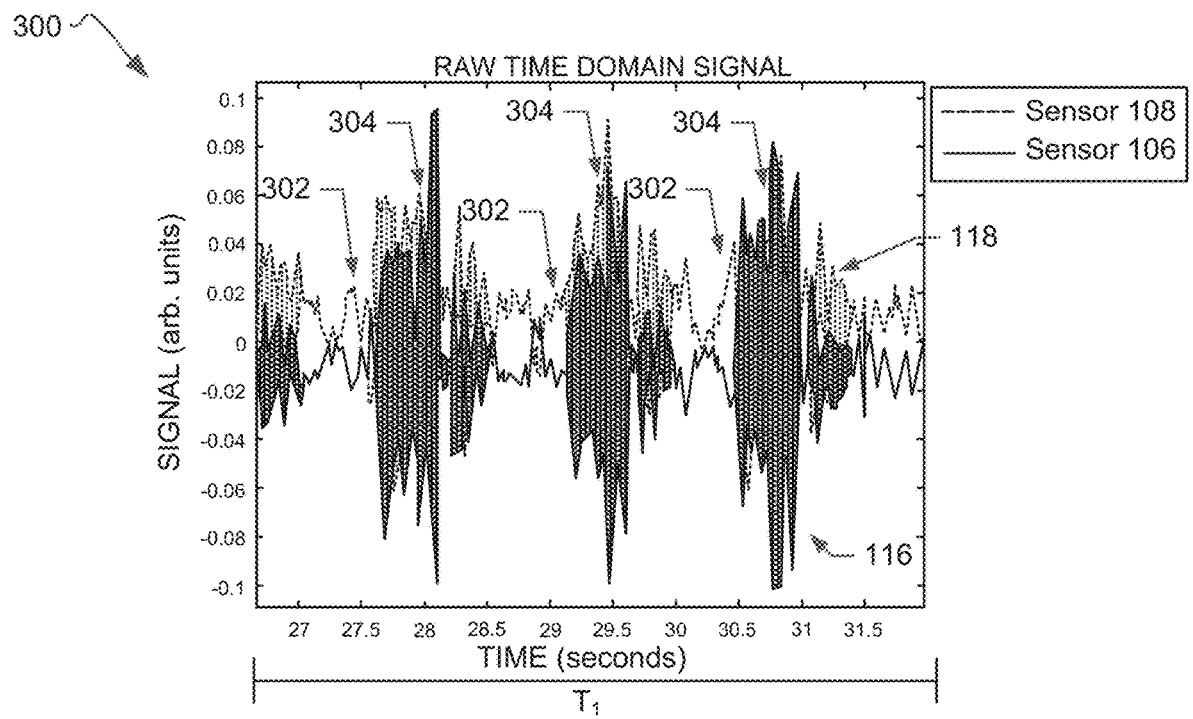
FIG. 3 is a graph illustrating first example acceleration data generated by a first sensor of the example bone conduction device of FIG. 1 and second example acceleration data generated by a second sensor of the example bone conduction device of FIG. 1.

FIG. 3 illustrates a graph 300 including example first acceleration data 116 and example second acceleration data 118 collected from a user (e.g., the user 104) wearing the example wearable device 102 of FIG. 1. In the example of FIG. 3, the first acceleration data 116 was generated by the first sensor 106 of the wearable device 102 disposed proximate to a first (e.g., right) side of the user's nose bridge and the second acceleration data 118 is generated by the second sensor 108 of the wearable device 102 disposed proximate to a second (e.g., left) side of the user's nose bridge. In the example of FIG. 3, the first acceleration data 116 and the second acceleration data 118 were collected during a first time period $t_1$ when the user 104 was rotating his or her head (e.g., to the right and left) while speaking. The signal data 116, 118 may be time-aligned by the example phase comparator 208 of FIG. 2.

As illustrated in FIG. 3, the time-aligned data 116, 118 of the graph 300 includes one or more out-of-phase portions 302 in which the first acceleration data 116 and the second acceleration data 118 are out-of-phase or substantially out-of-phase relative to one another. As also illustrated in FIG. 3, the graph 300 includes one or more in-phase portions 304 in which the first acceleration data 116 and the second acceleration data 118 are in-phase or substantially in-phase relative to one another.

Figure 4:
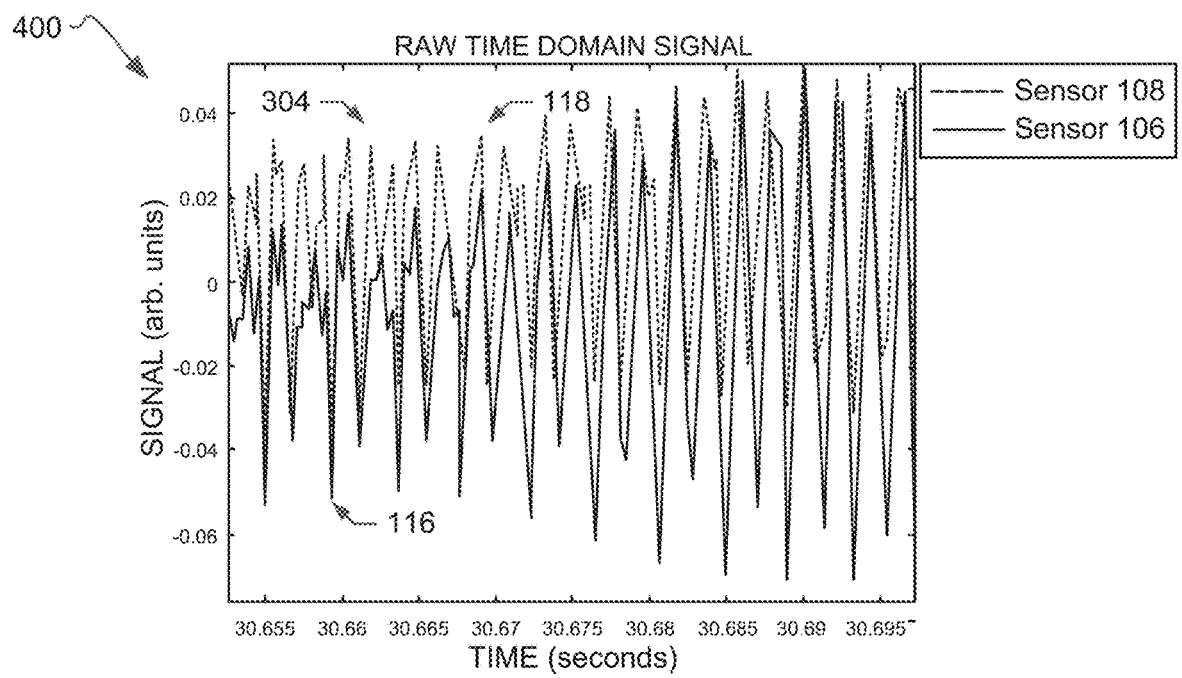
FIG. 4 is a graph illustrating portions of the respective first and second example acceleration data of FIG. 3.

FIG. 4 illustrates a graph 400 including an example in-phase portion 304 of the first acceleration data 116 and second acceleration data 118 in the graph 300 of FIG. 3 (e.g., collected over a portion of the time period $t_1$ of FIG. 3). As illustrated in FIG. 4, the first acceleration data 116 generated by the first sensor 106 of the wearable device 102 and the second acceleration data 118 generated by the second sensor 108 of the wearable device 102 are substantially in-phase relative to one another.

The example phase comparator 208 of the example bone conduction analyzer 130 of FIGS. 1 and 2 analyzes the signal data 116, 118 to determine if the signal data includes the in-phase portion(s) 304 and the out-of-phase portion(s) 302 of the first and second acceleration data 116, 118 generated by the respective sensors 106, 108 of the wearable device 102. As also discussed above, in some examples, if the phase comparator 208 determines that the acceleration data 116, 118 includes in-phase portion(s) 304 (e.g., indicative of sound data) and out-of-phase portion(s) 304 (e.g., indicative of motion data), the example signal modifier 212 of the bone conduction analyzer 130 of FIG. 2 modifies the acceleration data 116, 118 to remove or substantially remove motion data from the signal data. In some examples, the signal modifier 212 sums the acceleration signal data 116, 118 generated by the first and second sensors 106, 108 to cancel or substantially cancel the out-of-phase portion(s) 302, or the portions corresponding to the motion data, from the signal data.

Figure 5:
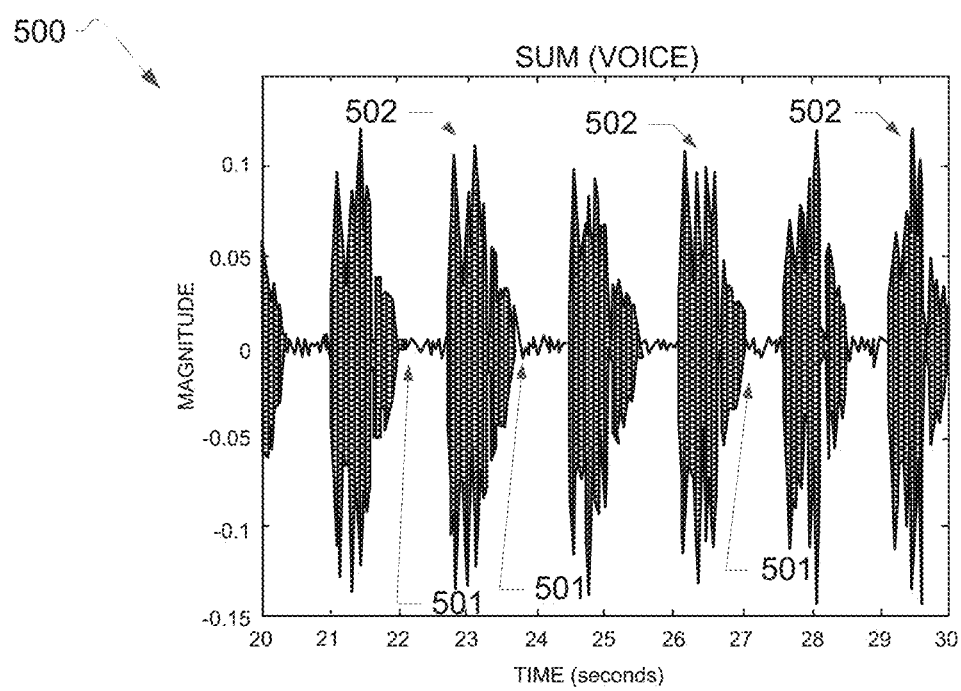
FIG. 5 is a graph illustrating the sum of the first and second example acceleration data of FIG. 3.

FIG. 5 illustrates an example graph 500 including the sum of the first acceleration data 116 and the second acceleration data 118 of FIG. 3. Summing the acceleration data can be performed by the example signal modifier 212 of FIG. 2 to generate modified signal data 214. As illustrated in FIG. 5, summing the acceleration data 118, 116 substantially reduces the magnitudes of the out-of-phase portion(s) of the acceleration data 116, 118, as represented by the motion data portion(s) 501 in FIG. 5. Put another way, summing the acceleration data 116, 118 substantially reduces or filters the motion data from the signal data. Further, summing the signal data 116, 118 increases the magnitudes of the in-phase portion(s) 304 of the signal data, as represented by the sound data portion(s) 502 of FIG. 5. Thus, summing the signal data enhances the sound data. As discussed above, the filtered signal data such as the data of FIG. 5 can be used by the speaker 114 of the wearable device 102 to provide an audio output that includes substantially less noise interference due to user motion.

Figure 6:
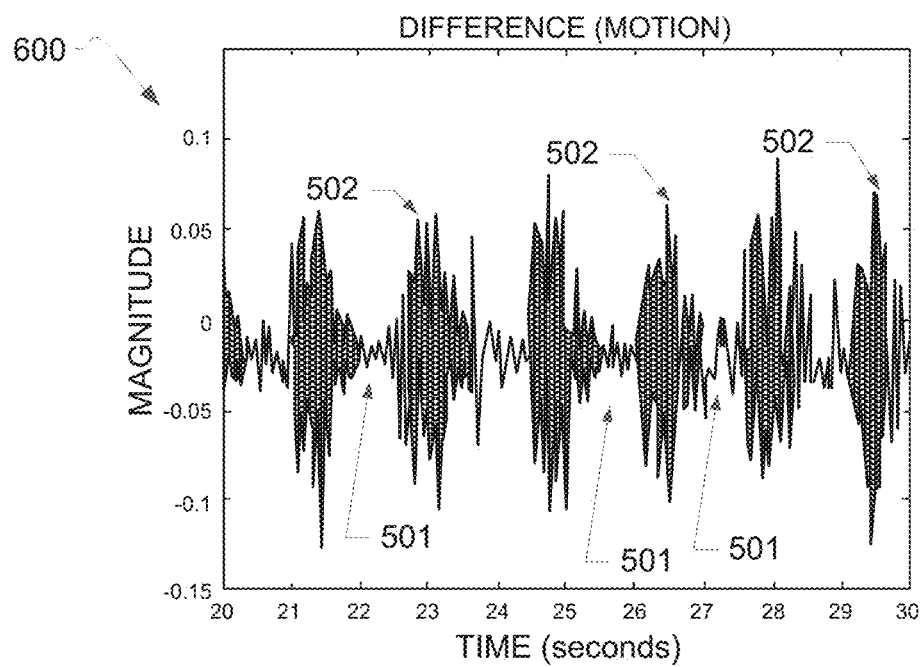
FIG. 6 is a graph illustrating the difference of the first and second example acceleration data of FIG. 3.

FIG. 6 illustrates an example graph 600 including the difference of the first acceleration data 116 and the second acceleration 118 of FIG. 3. As illustrated in FIG. 6, when the difference is taken between the first acceleration data 116 and the second acceleration data 118, the magnitude of the motion data portion(s) 501 (e.g., corresponding to the out-of-phase portions 302 of FIG. 3) is increased as compared to when the data is summed as in FIG. 5. As also illustrated in FIG. 6, the magnitude of the sound data portion(s) 502 (e.g., corresponding to the in-phase portions 304 of FIG. 3) is reduced as compared to when the data is summed as in FIG. 5. Thus, FIGS. 5 and 6 demonstrates that sound (e.g., voice) data generated by the sensors 106, 108 can be separated from motion data generated by the sensors 106, 108 due to movement by the user.

As discussed above, depending on wiring and/or orientation of the sensors 106, 108, the respective sum and difference of the signal data 116, 118 may generate the modified signal data including sound data (with motion data substantially removed) or motion data (with sound data substantially removed). Regardless of the conventions assigned to the sensors 106, 108, the signal modifier 212 of FIG. 2 can combine the signal data (e.g., add or subtract) to enhance the sound data or the motion data.

As discussed above, in some examples, the sensors 106, 108 of the example wearable device 102 of FIG. 1 generate data based on detection of sound(s) from external sound source(s) (e.g., the external sound source(s) 132). FIGS. 7-10 illustrate example graphs including data generated by the sensors 106, 108 of the example wearable device 102 due to exposure to sound from external sound source(s) disposed at different angles relative to a user (e.g., the user 104) wearing the wearable device 102. In particular, the graphs of FIGS. 7-10 include data generated when a 1 kHz sine wave was played from a speaker located approximately three feet from the user and positioned at the angles (−)60°, 0°, and (+)60° relative to the user's head, where 0° is measured substantially directly in front of the user's face (e.g., substantially aligned with the user's nose). According to this arrangement, the external sound source positioned at (−)60° relative to the user is disposed to the right of the user's nose (e.g., the nose 112 of the user 104 of FIG. 1) and the external sound source positioned at +60° relative to the user is disposed to the left of the user's nose.

Figure 7:
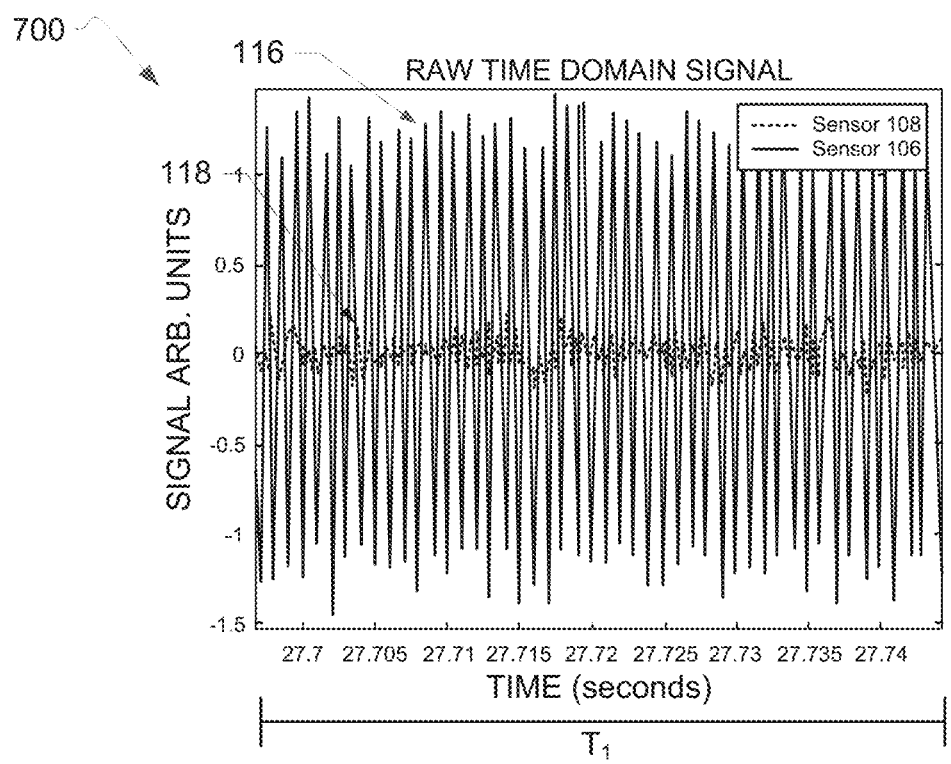
FIG. 7 is a graph illustrating example acceleration data generated by sensors of the example bone conduction device of FIG. 1.

FIG. 7 illustrates an example graph 700 including example first acceleration data 116 and example second acceleration data 118 collected from a user (e.g., the user 104) wearing the example wearable device 102 of FIG. 1. In the example of FIG. 7, the first acceleration data 116 was generated by the first sensor 106 of the wearable device 102 disposed proximate to the right side of the user's nose bridge and the second acceleration data 118 was generated by the second sensor 108 of the wearable device 102 disposed proximate to the left side of the user's nose bridge. In the example of FIG. 7, the first acceleration data 116 and the second acceleration data 118 were collected during a first time period $t_1$ when a 1 kHz sine wave was played from a speaker positioned at approximately (−) 60° relative to the user's face (e.g., nose), or to the right of the user 104 of FIG. 1. As illustrated in FIG. 7, the magnitude of the acceleration data 116 generated by the first sensor 106, or the sensor disposed on the right side of the user's nose bridge is greater than the magnitude of the acceleration data 118 generated by the second sensor 108, or the sensor disposed on the left side of the user's nose bridge.

Figure 8:
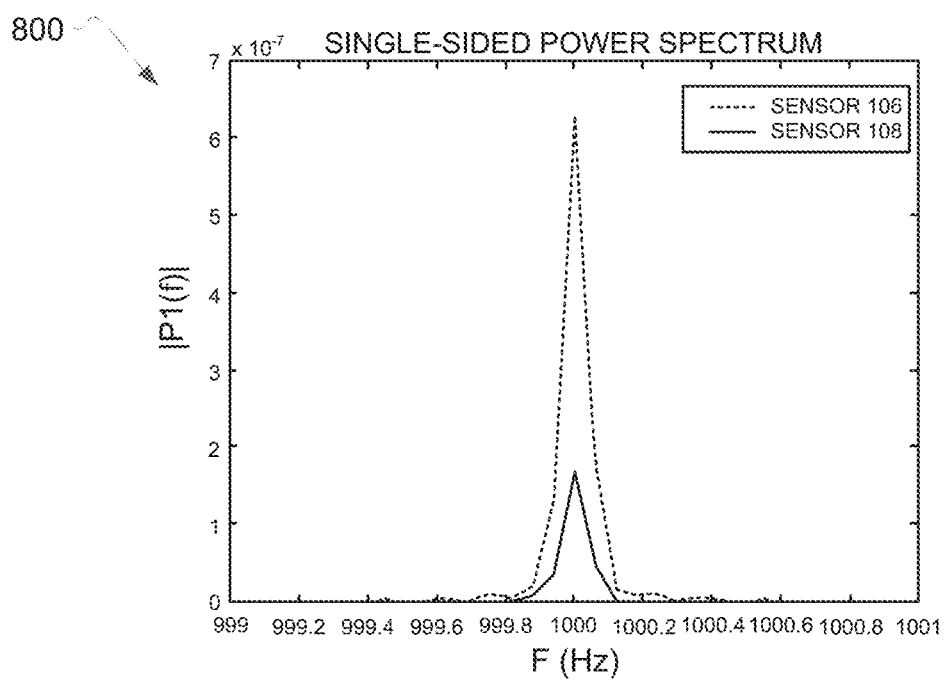
FIG. 8 is a graph illustrating an example power spectrum based on the example acceleration data of FIG. 7

FIG. 8 illustrates an example graph 800 including a single-sided power spectrum derived from the acceleration data 116, 118 of FIG. 7. As illustrated in FIG. 8, the magnitude of the data generated by the first sensor 106, or the sensor disposed on the same side of the user as the external sound source providing the sound (e.g., the user's right side), is greater than the magnitude of the data generated by the second sensor 108, or the sensor opposite the side on which the external sound source is disposed.

Figure 9:
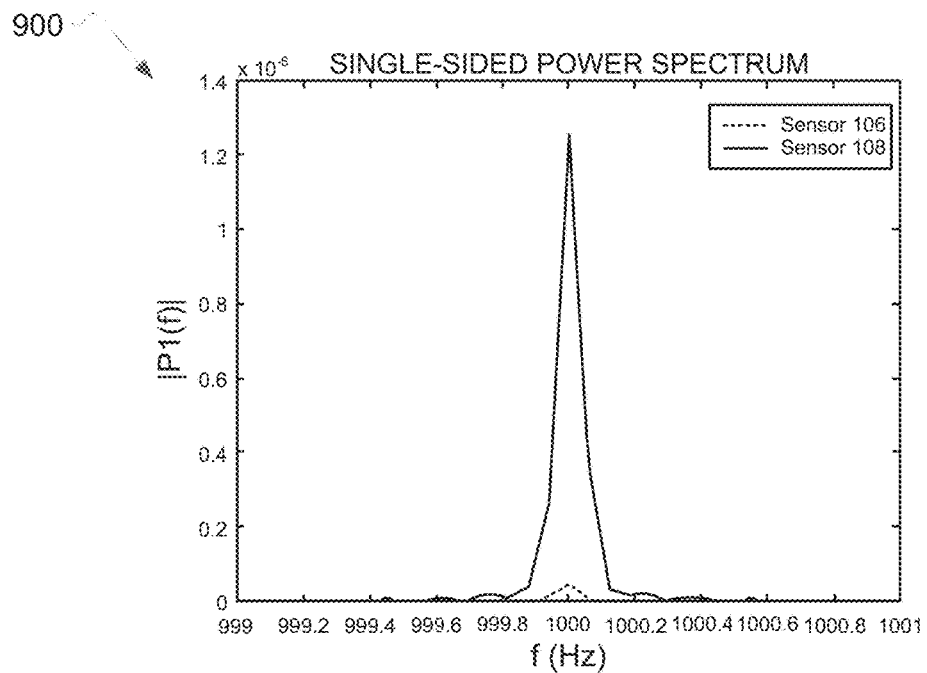
FIG. 9 is a graph illustrating an example power spectrum based on example acceleration data.

FIG. 9 illustrates an example graph 900 including a single-sided power spectrum based on example first acceleration data 116 and example second acceleration data 118 collected from a user (e.g., the user 104) wearing the example wearable device 102 of FIG. 1. In the example of FIG. 9, the sensors 106, 108 generate the acceleration data based on sound from an external sound source positioned at approximately (+)60° relative to the user's face (e.g., nose), or to the left of the user 104 of FIG. 1. As illustrated in FIG. 9, the magnitude of the acceleration data generated by the second sensor 108, or the sensor disposed on the left side of the user's nose bridge, is greater than the magnitude of the acceleration data generated by the first sensor 106, or the sensor disposed on the right side of the user's nose bridge. Thus, as illustrated in FIG. 8 (e.g., corresponding to an external sound source at (−)60° relative to the user) and FIG. 9 (e.g., corresponding to an external sound source at (+)60° relative to the user), the magnitude of the respective signal data collected by the respective sensors 106, 108 is substantially unequal when the external sound source is disposed to one of the sides of the user of the wearable device 102.

Figure 10:
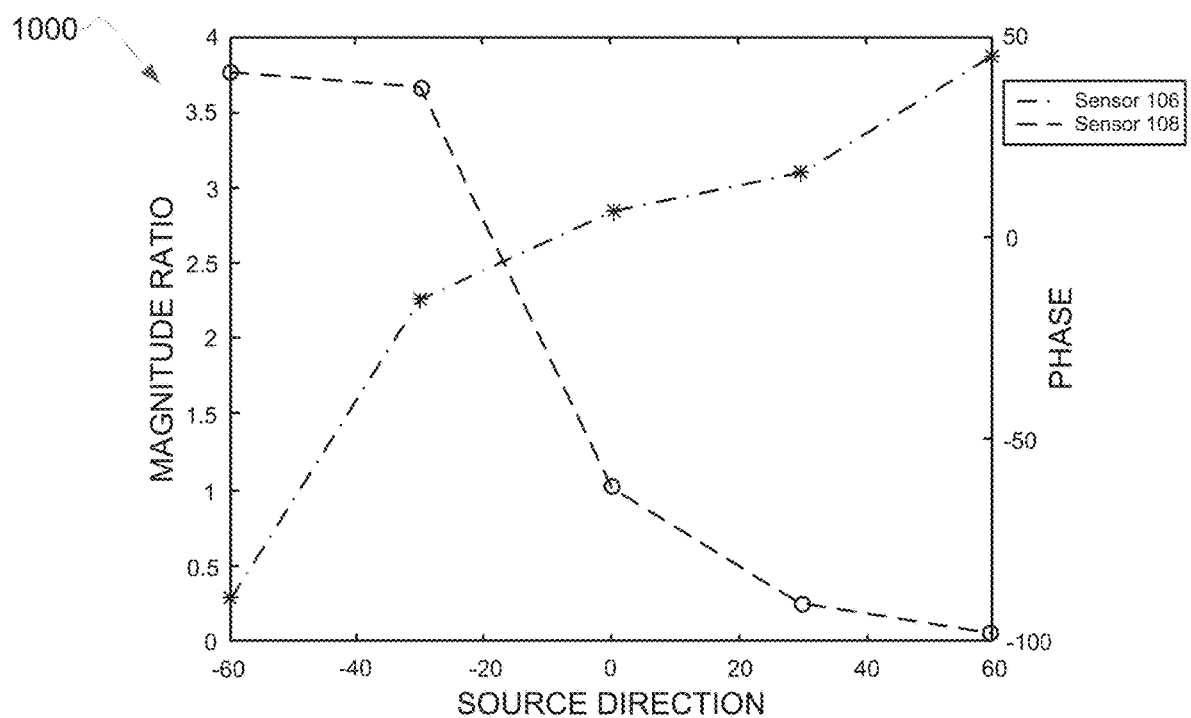
FIG. 10 is a graph illustrating an example relationship between position of an external sound source and magnitude and phase of acceleration data generated by sensors of the example bone conduction device of FIG. 1 as a result of sound originating from the external sound source.

FIG. 10 illustrates an example graph 1000 showing the relationship of magnitude and phase of signal data generated by the respective sensors 106, 108 of the wearable device based on the position of an external sound source relative to the user of the wearable device 102. As shown in FIG. 10, the signal data generated by the respective sensors 106, 108 is out-of-phase and has unequal magnitude when the external sound source is disposed to the right or left side of the user (e.g., at −60°, −30°, +30°, or +60° relative to the user). As discussed above, the sound source identifier 218 of the example bone conduction analyzer 130 of FIG. 2 uses the different magnitude and/or phase characteristics of the signal data to identify the sound as originating from an external source (e.g., based on the source identification rules 220) and to detect the direction in which the external sound was generated relative to the user. Thus, FIGS. 7-10 illustrate that characteristics of the signal data such as phase and magnitude can be used by the example bone conduction analyzer 130 of FIGS. 1 and 2 to identify sound(s) as originating from external sound source(s) or from the user and, in examples in which the sound(s) originate from external sound source(s), to detect the direction in which the external sound(s) were generated relative to the user.

Figure 11:
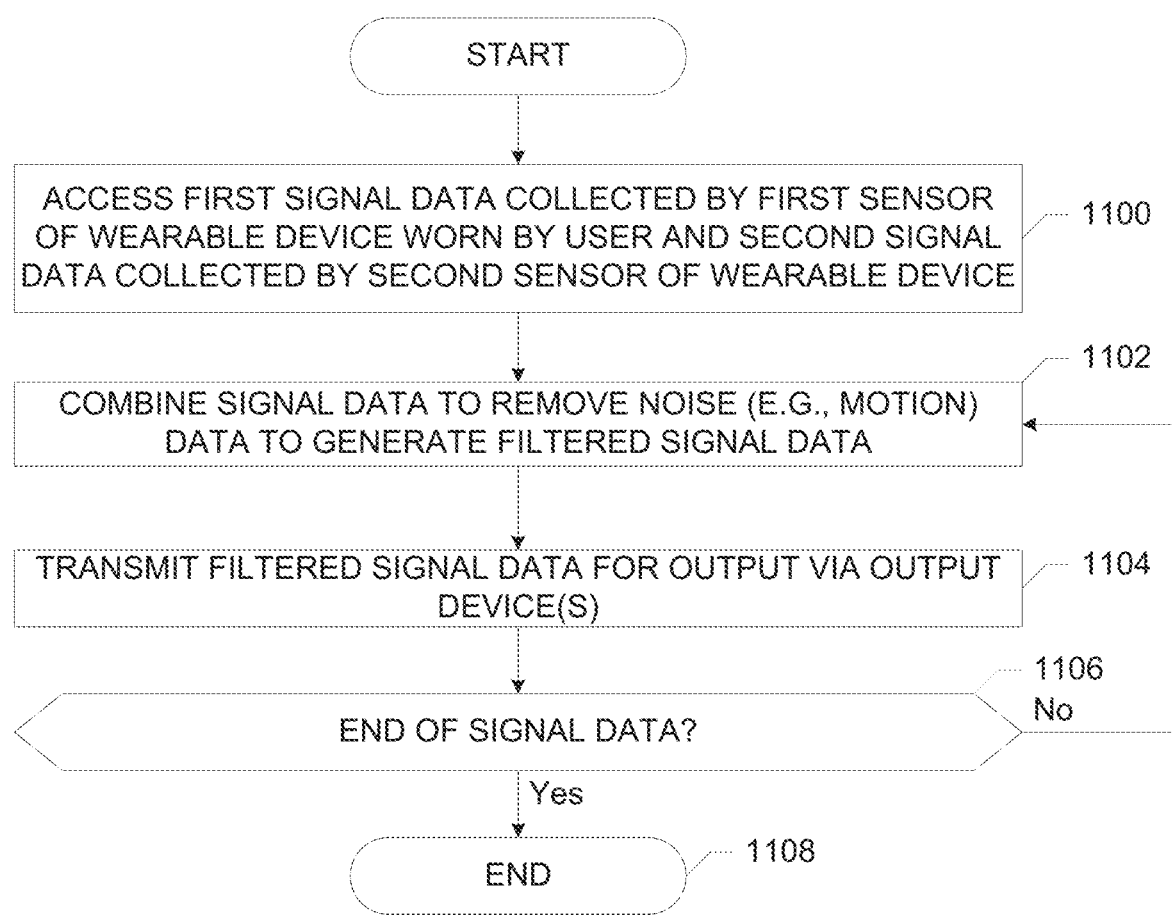
FIG. 11 is a flowchart representative of example machine readable instructions that may be executed to implement the example system of FIGS. 1 and/or 2.
Figure 12:
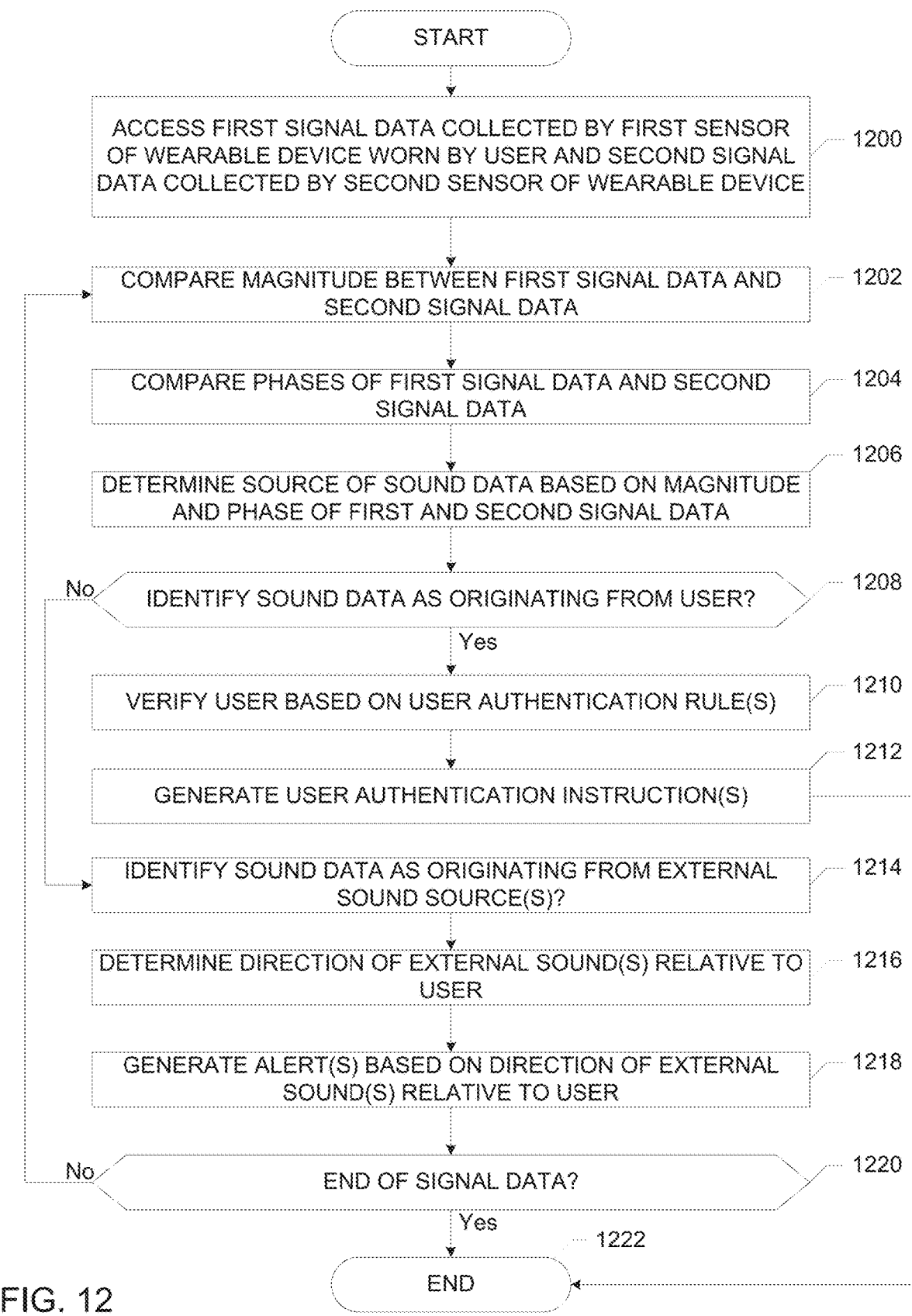
FIG. 12 is a flowchart representative of example machine readable instructions that may be executed to implement the example system of FIGS. 1 and/or 2.

Flowcharts representative of example hardware logic or machine readable instructions for implementing the example system of FIGS. 1 and/or 2 are shown in FIGS. 11 and 12. The machine readable instructions may a program or a portion of a program for execution by a processor such as the processor such as the bone conduction analyzer 130 shown in the example processor platform 1300 discussed below in connection with FIG. 13. The program may be embodied in software stored on a non-transitory computer readable storage medium such as a CD-ROM, a floppy disk, a hard drive, a DVD, a Blu-ray disk, or a memory associated with the bone conduction analyzer 130, but the entire program and/or parts thereof could alternatively be executed by a device other than the bone conduction analyzer 130 and/or embodied in firmware or dedicated hardware. Further, although the example program is described with reference to the flowcharts illustrated in FIGS. 11 and 12, many other methods of implementing the example system may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example processes of FIGS. 11 and 12 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, and (6) B with C.

FIG. 11 is a flowchart of example machine readable instructions that, when executed, cause the example bone conduction analyzer 130 of FIGS. 1 and/or 2 to identify sound (e.g., voice) data generated by a user (e.g., the user 104) and motion data based on sensor data (e.g., the acceleration data 116, 118) and to remove or substantially remove the motion data. In the example of FIG. 11, signal data can be collected via sensors 106, 108 of the wearable device 102 of FIG. 1. Although the example instructions FIG. 11 are discussed in connection with sound data, in other examples, the instructions of FIG. 11 can be used to cancel, for example, motion data from breathing data detected by the sensors of the wearable device 102 to generate filtered breathing data.

The example instructions of FIG. 11 can be executed by the bone conduction analyzer 130 of FIGS. 1 and/or 2. The bone conduction analyzer 130 of FIGS. 1 and/or 2 can be implemented by one or more processors of the wearable device 102, the user device 126, and/or the cloud-based device 128. In some examples, some of the bone conduction data analysis is implemented by the bone conduction analyzer 130 via a cloud-computing environment and one or more other parts of the analysis are implemented by the processor of the wearable device 102 and/or the processor of the user device 126. The instructions of FIG. 11 can be executed in substantially real-time as the signal data is generated and received by the bone conduction analyzer 130 or at some time after the signal data is generated. In some examples, the location(s) at which the analysis is performed by the bone conduction analyzer 130 is based on whether the analysis is to be performed in substantially real-time as the signal data is generated or whether the analysis is to be performed at a later time. For example, if the analysis is to be performed in substantially real-time as the signal data is generated, the analysis may be performed by the bone conduction analyzer 130 at the wearable device 102. In other examples, if the analysis is to be performed at a later time and/or if the signal data is to be transferred to the bone conduction analyzer 130 at a later time, then the analysis may be performed at the user device 126.

The example phase comparator 208 of FIG. 2 accesses first signal data 116 (e.g., acceleration data) collected by the first sensor 106 of the wearable device 102 of FIG. 1 and second signal data 118 collected by the second sensor 108 of the wearable device 102 (block 1100). For example, the bone conduction analyzer 130 accesses signal data 116, 118 generated over time from the user 104 wearing the wearable device 102 including the sensors 106, 108 (e.g., accelerometers). In some examples, the signal data 116, 118 is converted by the A/D converter 202 of bone conduction analyzer 130 to digital signal data. In other examples, the acceleration data 116, 118 is received by the bone conduction analyzer 130 as digital signal data (e.g., after being converted by another processor). In other examples, the acceleration data 116, 118 is processed by the bone conduction analyzer 130 as analog data.

The example signal modifier 212 of FIG. 2 removes noise (e.g., motion data) from the signal data by combining the signal data (block 1102). For example, the phase comparator 208 aligns the first acceleration data 116 and the second acceleration data 118 over the time period for which the data was collected. The signal modifier 212 of FIG. 2 removes or substantially removes the motion data from the acceleration data 116, 118. For example, the signal modifier 212 sums or subtracts the time-aligned signal data 116, 118 to cancel or substantially cancel the motion data from the signal data 116, 118 based on whether motion data is associated with the in-phase portions of the data or the out-of-phase portions of the time-aligned acceleration data 116, 118. As a result of the combining of the acceleration data 116, 118, the signal modifier 212 generates modified or filtered signal data 214.

In the example of FIG. 11, the communicator 216 of the bone conduction analyzer 130 transmits the filtered signal data 214 for output via one or more output devices (block 1104). For example, the communicator 216 can transmit the filtered signal data 214 for output via the speaker 114 of the wearable device 102 of FIG. 1.

The example bone conduction analyzer 130 continues to analyze the signal data 116, 118 generated by the respective sensors 106, 108 with respect to phase differences and combine the signal data 116, 118 (block 1106). If there is no further signal data 116, 118 to be analyzed, the instructions of FIG. 11 end (block 1108).

FIG. 12 is a flowchart of example machine readable instructions that, when executed, cause the example bone conduction analyzer 130 of FIGS. 1 and/or 2 to determine whether sound data originated from a user (e.g., the user 104) of the wearable device or an external sound source (e.g., the external sound source 132 of FIG. 1) based on sensor data (e.g., the acceleration data 116, 118). If the bone conduction analyzer 130 determines that the sound data originated from an external sound source, the example instructions of FIG. 12 cause the bone conduction analyzer 130 to determine a direction in which the external sound originated relative to the user (e.g., to the left or right of the user). In the example of FIG. 12, signal data can be collected via sensors 106, 108 of the wearable device 102 of FIG. 1.

The example instructions of FIG. 12 can be executed by the bone conduction analyzer 130 of FIGS. 1 and/or 2. The bone conduction analyzer 130 of FIGS. 1 and/or 2 can be implemented by one or more processors of the wearable device 102, the user device 126, and/or the cloud-based device 128. In some examples, some of the bone conduction data analysis is implemented by the bone conduction analyzer 130 via a cloud-computing environment and one or more other parts of the analysis are implemented by the processor of the wearable device 102 and/or the processor of the user device 126. The instructions of FIG. 12 can be executed in substantially real-time as the signal data is generated and received by the bone conduction analyzer 130 or at some time after the signal data is generated.

The example sound source identifier 218 of FIG. 2 accesses first signal data 116 (e.g., acceleration data) collected by the first sensor 106 of the wearable device 102 of FIG. 1 and second signal data 118 (e.g., acceleration data) collected by the second sensor 108 of the wearable device 102 (block 1200). For example, the bone conduction analyzer 130 access signal data 116, 118 generated over time from the user 104 wearing the wearable device 102 including the sensors 106, 108 (e.g., accelerometers). In some examples, the signal data 116, 118 is converted by the A/D converter 202 of bone conduction analyzer 130 to digital signal data. In other examples, the signal data 116, 118 is received by the bone conduction analyzer 130 as digital signal data (e.g., after being converted by another processor).

The magnitude comparator 219 of the example bone conduction analyzer 130 of FIG. 2 compares the magnitude of the first signal data 116 generated by the first sensor 106 and the magnitude of the second signal data 118 generated by the second sensor 108 (block 1202). In some examples, the sound frequency domain converter 210 converts the signal data 116, 118 from the time domain and the magnitude comparator 219 analyzes the magnitude in the frequency domain.

The example phase comparator 208 compares the phases of the signal data 116, 118 (block 1204). For example, the phase comparator 208 identifies whether the signal data 116, 118 includes portions that are in-phase or out-of-phase between the respective signal data 116, 118. The phase comparator 208 can analyze the signal data 116, 118 in the time domain or the frequency domain.

In the example of FIG. 12, the sound source identifier 218 determines a source of the sound data based on the comparisons of magnitudes and phase of the first and second signal data 116, 118 (block 1206). For example, the sound source identifier 218 applies the source identification rule(s) 220 to determine if the signal data 116, 118 was generated by the sensors 106, 108 in response to sound (e.g., speech) produced by the user of the wearable device 102 or in response to sound(s) generated by external sound source(s) (e.g., other individual(s)).

As an example, the source identification rule(s) 220 can indicate that when the first and second signal data 116, 118 include out-of-phase portion(s) having substantially unequal magnitudes, then the sound data originated from an external sound source 132. The source identification rule(s) 220 can indicate that when the first and second signal data 116, 118 include in-phase portion(s) having substantially equal magnitudes, than the sound data originated from the user (e.g., wearer) of the wearable device 102. The source identification rule(s) 220 can indicate that when portion(s) of the first and second acceleration data 116, 118 are in-phase and have magnitudes falling below a particular threshold), then the sound data originated from an external sound source. The source identification rule(s) 220 can be defined by user inputs and stored in the database 200 of the bone conduction analyzer 130 of FIG. 1.

In the example of FIG. 12, if the sound source identifier 218 determines that the sound originated from the user of the wearable device 102 (block 1208), the user authorization verifier 224 of the bone conduction analyzer 130 authenticates or verifies the user of the wearable device 102 (block 1210). For example, the user authorization verifier 224 can verify the user based on user authentication rule(s) 228 to control user access one or more user applications 134 implemented by, for example, processor(s) of the wearable device, the wearable or non-wearable device 126, etc. The user authentication rule(s) 228 can include rules for authenticating the user based on, for example, one or more features of the sound data, such as magnitude values relative to predefined thresholds. The user authentication rule(s) 228 can be defined by user inputs and stored in the database 200 of the bone conduction analyzer 130 of FIG. 1.

The example user authorization verifier 224 generates user authorization instruction(s) 226 based on the authentication of the user (block 1212). The communicator 216 can transmit the instruction(s) to the output device(s) to enable the user to access, for example, one or more user applications 134 via the output device(s).

In the example of FIG. 12, if the sound source identifier 218 determines that the sound data originated from external sound source(s) 132 (block 1214), the sound source identifier 218 determines a direction in which the external sound(s) originated relative to the user (block 1216). For example, based on the comparison of the magnitudes of the first and second signal data 116, 118, the sound source identifier 218 can determine whether the external sound(s) originated proximate to the side of the user on which the first sensor 106 is disposed (e.g., the user's right side) or proximate to the side of the user on which the second sensor 108 is disposed (e.g., the user's left side). The sound source identifier 218 can apply the sound source identification rule(s) 220 to identify the direction of the external sound(s) relative to the user based on, for example, which sensor 106, 108 generates signal data having larger magnitude.

The example alert generator 221 of the bone conduction analyzer 130 activates one or more output devices (e.g. the wearable device 102, the wearable or non-wearable device 126) to generate alert(s) 222 based on the determination of the direction of the external sound(s) relative to the user (block 1218). The alert(s) 222 can include audio, visual, and/or tactile alerts that serve to inform the user as to the direction of the external sound(s). The communicator 216 can transmit instructions for the output device(s) to generate the alert(s) 222 for presentation to the user.

The example bone conduction analyzer 130 continues to analyze the signal data 116, 118 to distinguish between sound data generated by the user and sound data generated by external sound source(s) (block 1220). If there is no further signal data to be analyzed, the instructions of FIG. 12 end (block 1222).

Figure 13:
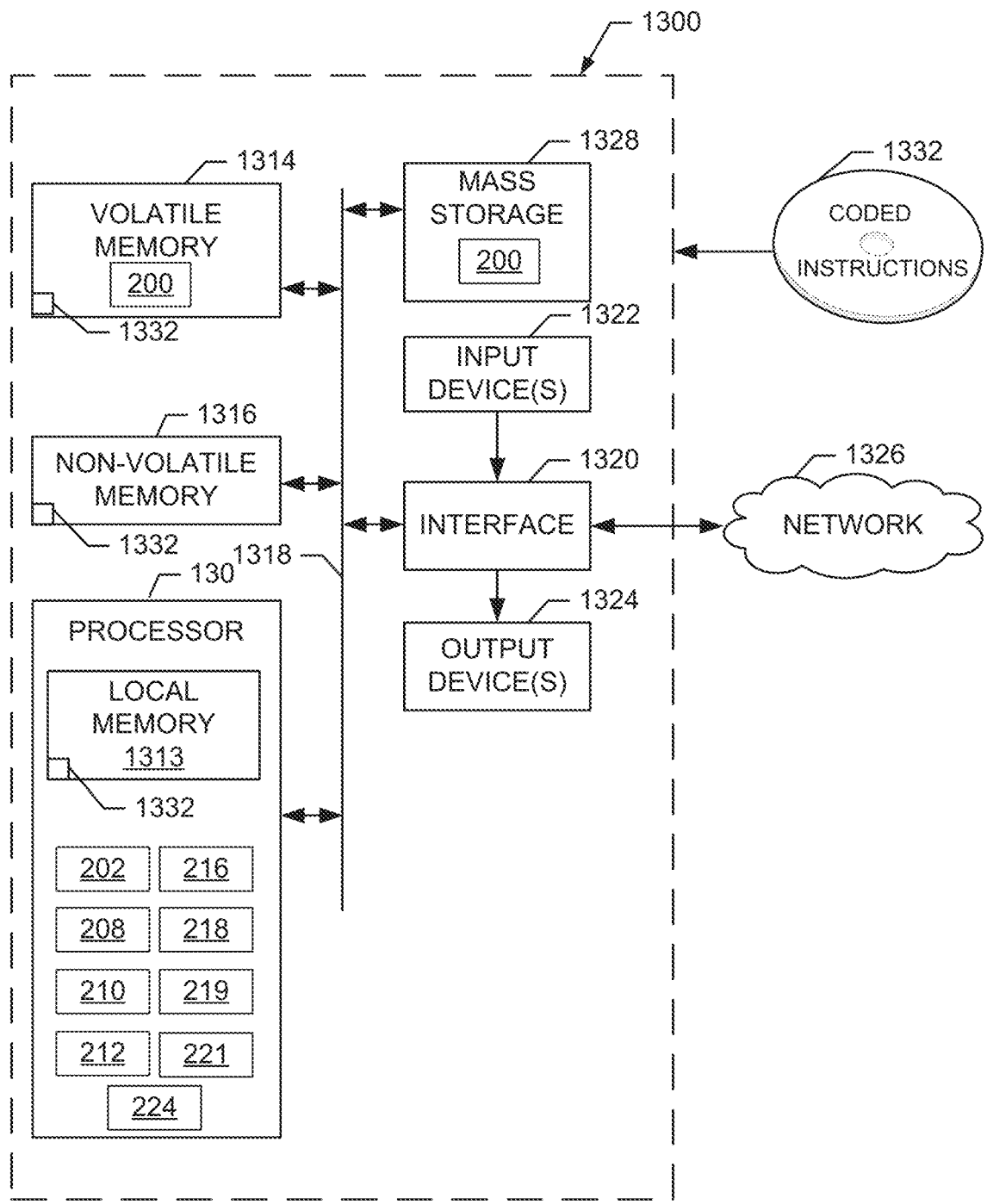
FIG. 13 is a block diagram of an example processor platform constructed to execute the example instructions of FIGS. 11 and/or 12 to implement the example system of FIGS. 1 and/or 2.

FIG. 13 is a block diagram of an example processor platform 1300 structured to execute the instructions of FIGS. 11 and/or 12 to implement the example system of FIGS. 1 and/or 2. The processor platform 1300 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a headset or other wearable device, or any other type of computing device.

The processor platform 1300 of the illustrated example includes a processor implement the bone conduction analyzer 130. The processor 130 of the illustrated example is hardware. For example, the processor 130 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 130 implements the example A/D converter 202, the example phase comparator 208, the example frequency domain converter 210, the example signal modifier 212, the example communicator 216, the example sound source identifier 218, the example magnitude comparator 219, the example alert generator 221, and the example user authorization verifier 224.

The processor 130 of the illustrated example includes a local memory 1213 (e.g., a cache). The processor 130 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1316 may be implemented by flash memory and/or any other desired type of memory device. Access to the main memory 1314, 1316 is controlled by a memory controller. The database 200 of the processor 130 may be implemented by the main memory 1314, 1316 and/or the local memory 1313.

The processor platform 1300 of the illustrated example also includes an interface circuit 1320. The interface circuit 1320 may be implemented by any type of interface standard, such as an Ethernet interface, a universal serial bus (USB), a Bluetooth® interface, a near field communication (NFC) interface, and/or a PCI express interface.

In the illustrated example, one or more input devices 1322 are connected to the interface circuit 1320. The input device(s) 1322 permit(s) a user to enter data and/or commands into the processor 1312. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 1320 of the illustrated example, thus, typically includes a graphics driver card, a graphics driver chip and/or a graphics driver processor. Alerts of the alert generator 221 and/or instructions of the user authorization verifier 224 may be used to drive one or more of the output devices.

The interface circuit 1320 of the illustrated example also includes a communication device such as a transmitter, a receiver, a transceiver, a modem, a residential gateway, a wireless access point, and/or a network interface card to facilitate exchange of data with external machines (e.g., computing devices of any kind) via a network 1326. The communication can be via, for example, Ethernet connection, a digital subscriber line (DSL connection), a telephone line connection, coaxial cable system, a satellite system, a line-of-site wireless system, a cellular telephone system, etc.

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, redundant array of independent disks (RAID) systems, and digital versatile disk (DVD) drives. Some or all of the database 200 may be stored in the mass storage device 1328.

The machine executable instructions 1332 of FIGS. 11 and/or 12 may be stored in the mass storage device 1328, in the volatile memory 1314, in the non-volatile memory 1316, and/or on a removable non-transitory computer readable storage medium such as a CD or DVD.

From the foregoing, it will be appreciated that example methods, systems, and have been disclosed to detect whether sound data originated from a user of a bone conduction device or from an external sound source (e.g., another individual who is speaking). Based on the determination of the sound source as originating from the user or an external source, some disclosed examples regulate user access to, for example, user application(s) executed by user device(s) to prevent unauthorized access to the user application(s) (e.g., by individuals who are not the user of the wearable device). Some disclosed examples identify a direction in which the external sound(s) originated relative to the user and provide for informational alerts that can assist, for example, a visually impaired user of the wearable device.

Some disclosed examples distinguish between sound (e.g., voice) data and motion data generated due to user movement, such as movement of the user's head while speaking and/or listening. Disclosed examples provide for efficient cancellation of motion data from the signal data due to intentional and/or unintentional movement by the user to improve a quality of data output via, for example, an acoustic audio speaker and/or a bone conduction speaker.

The following is a non-exclusive list of examples disclosed herein. Other examples may be included above. In addition, any of the examples disclosed herein can be considered in whole or in part, and/or modified in other ways.

Example 1 includes a wearable device includes a first sensor positioned to generate first vibration information from a bone structure of a user; a second sensor positioned to generate second vibration information from the bone structure of the user, the first vibration information and the second vibration information including sound data and motion data, the motion data indicative of a motion by the user; a signal modifier to generate a modified signal including the sound data based on the first vibration information and the second vibration information; and a communicator to transmit the modified signal for output via a speaker.

Example 2 includes the wearable device as defined in example 1, wherein the signal modifier is to sum the first vibration information and the second vibration information to generate the modified signal.

Example 3 includes the wearable device as defined in examples 1 or 2, wherein the first sensor is disposed proximate to a first side of a nasal bridge of the user and the second sensor is disposed proximate to a second side of the nasal bridge of the user opposite the first side.

Example 4 includes the wearable device as defined in examples 1 or 2, wherein the motion data is associated with motion of a head of the user.

Example 5 includes an apparatus including a signal modifier to separate sound data from motion data based on first bone vibration information generated by a first sensor coupled to a user and second bone vibration information generated by a second sensor coupled to the user, the first and second bone vibration information including the sound data and the motion data, the motion data indicative of a motion by the user. The signal modifier is to generate modified signal data based on the separation of the sound data and the motion data. The example apparatus includes a communicator to transit the modified data to a user device.

Example 6 includes the apparatus as defined in example 5, further including a phase comparator to compare a phase of a portion of the first bone vibration information to a phase of a portion of the second bone vibration information.

Example 7 includes the apparatus as defined in example 6, wherein if the phases of the respective portions of the first and second bone vibration information are in-phase, the portions are associated with the sound data.

Example 8 includes the apparatus as defined in example 5, wherein the signal modifier is to separate the sound data from the motion data by one of adding the first bone vibration information and the second bone vibration information or subtracting the first bone vibration information and the second bone vibration information.

Example 9 includes the apparatus as defined in examples 5 or 6, further including a sound source identifier to identify the sound data as associated with a vocal activity performed by the user.

Example 10 includes the apparatus as defined in example 9, wherein the vocal activity is speech by the user.

Example 11 includes the apparatus as defined in any of examples 5, 6, or 8, wherein the first bone vibration information is indicative of nasal bone vibrations.

Example 12 includes at least one non-transitory computer readable storage medium comprising instructions, that, when executed, cause a machine to separate sound data from motion data based on first bone vibration information generated by a first sensor coupled to a user and second bone vibration information generated by a second sensor coupled to the user, the first and second bone vibration information including the sound data and the motion data, the motion data indicative of a motion by the user; generate modified signal data based on the separation of the sound data and the motion data; and transit the modified data to a user device.

Example 13 includes at least one non-transitory computer readable storage medium as defined in example 12, wherein the instructions further cause the machine to compare a phase of a portion of the first bone vibration information to a phase of a portion of the second bone vibration information.

Example 14 includes at least one non-transitory computer readable storage medium as defined in examples 12 or 13, wherein the instructions further cause the machine to separate the sound data from the motion data by one of adding the first bone vibration information and the second bone vibration information or subtracting the first bone vibration information and the second bone vibration information.

Example 15 includes at least one non-transitory computer readable storage medium comprising instructions, that, when executed, cause a machine to identify sound data as based on first vibration signal data generated via a first sensor from a bone structure of a user and second vibration signal data generated via a second sensor from the bone structure of the user; classify the sound data as originating from one of the user or an external sound source; generate user authorization instructions based on the classification of the sound data as originating from the user or the external sound source; and activate an output device to control access to a user application based on the user authorization instructions.

Example 16 includes the at least one non-transitory computer readable storage medium as defined in example 15, wherein the instructions further cause the machine to classify the sound data as originating from one of the user or the external sound source based on a comparisons of phase of the respective first vibration signal data and the second vibration signal data.

Example 17 includes the at least one non-transitory computer readable storage medium as defined in example 16, wherein the instructions further cause the machine to classify the sound data as originating from one of the user or the external sound source based on a comparison of the magnitude of the first vibration signal data and the second vibration signal data relative to a threshold.

Example 18 includes the at least one non-transitory computer readable storage medium as defined in example 15, wherein the user authorization instructions are to enable the user to access the user application based on the classification of the sound data as originating from the user.

Example 19 includes the at least non-transitory computer readable storage medium as defined in example 15, wherein the instructions further cause the machine to determine a direction in which the sound data originated relative to the user based on the classification of the sound data as originating from the external sound source.

Example 20 includes the at least one non-transitory computer readable storage medium as defined in example 19, wherein the instructions further cause the machine to compare a magnitude of the first vibration signal data to a magnitude of the second vibration signal data to determine the direction in which the sound data originated relative to the user.

Example 21 includes the at least one non-transitory computer readable storage medium as defined in example 20, wherein the instructions further cause the machine to identify the sound data as originating proximate to the first sensor if the magnitude of the first vibration signal data is greater than the magnitude of the second vibration signal data.

Example 22 includes the at least one non-transitory computer readable storage medium as defined in example 19, wherein the instructions further cause the machine to activate the output device to generate at least one of an audible, tactile, or visual alert based on the determination of the direction from which the sound originated.

Example 23 includes the at least one non-transitory computer readable storage medium as defined in example 15, wherein the instructions further cause the machine to identify noise data in the sound data based on the classification of the sound data as originating from the user and remove the noise data from the sound data.

Example 24 includes a method including separating sound data from motion data based on first bone vibration information generated by a first sensor coupled to a user and second bone vibration information generated by a second sensor coupled to the user, the first and second bone vibration information including the sound data and the motion data, the motion data indicative of a motion by the user and transmitting, by executing an instruction with the processor, the filtered signal data for output via a speaker.

Example 25 includes the method as defined in example 24, further including comparing a phase of a portion of the first bone vibration information to a phase of a portion of the second bone vibration information.

Example 26 includes the method as defined in example 24, wherein the separating of the sound data from the motion data includes one of adding the first bone vibration information and the second bone vibration information or subtracting the first bone vibration information and the second bone vibration information.

Example 27 includes the method as defined in example 24, wherein the first bone vibration information is indicative of nasal bone vibrations.

Example 28 includes an apparatus including means for identifying a source of sound data based on bone vibration information obtained from a nasal bridge of a user; means for generating an alert when the means for identifying identifies the sound data as originating from an external sound source; and means for removing motion data indicative of a motion of the user from the sound data when the means for identifying identifies the sound data as originating from the user.

Example 29 includes the apparatus of example 28, further including means for authenticating the user to access a user application of a user device based on the identification of the sound data as originating from the user. Example 30 includes the apparatus of example 28, wherein vibration data includes first bone vibration data and second bone vibration data and the means for removing data includes a signal modifier to one of sum or subtract the first vibration data and the second vibration data.

Example 31 includes the apparatus of example 28, wherein the means for identifying the source of the sound data is to determine a position of the external sound source relative to the user based on the identification of the sound data as originating from the external sound source and the means for generating the alert is to generated the alert based on the position of the external sound source.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
memory;
machine-readable instructions; and
processor circuitry to execute the machine-readable instructions to:
associate a vibration signal with motion based on a first portion of the vibration signal being in-phase with a second portion of the vibration signal, the vibration signal transmitted via a bone structure of a user;
associate the vibration signal with voice based on the first portion of the vibration signal being out-of-phase with the second portion of the vibration signal;
permit access to a user application based on the association of the vibration signal with the voice; and
deny access to the user application based on the association of the vibration signal with the motion.

2. The apparatus of claim 1, wherein the bone structure includes a first bone structure and a second bone structure and the vibration signal includes a first vibration signal associated the first bone structure and a second vibration signal associated with the second bone structure, the first vibration signal including the first portion and the second vibration signal including the second portion.

3. The apparatus of claim 1, wherein the motion is indicative of movement of a head of the user.

4. The apparatus of claim 1, wherein the processor circuitry is to associate the vibration signal with the voice based on a magnitude of the vibration signal.

5. The apparatus of claim 4, wherein the processor circuitry is to determine that the vibration signal originates from the user based on the magnitude of the vibration signal relative to a threshold.

6. The apparatus of claim 1, wherein the processor circuitry is to associate the vibration signal with the voice by identifying a speech pattern characteristic represented in the vibration signal.

7. An apparatus comprising:
a first sensor to output a first vibration signal associated with a first bone structure of a user;
a second sensor to output a second vibration signal associated with a second bone structure of the user;
memory;
machine-readable instructions; and
processor circuitry to execute the instructions to:
detect one or more of (a) sound originating from the user or (b) motion of the user based on the first vibration signal and the second vibration signal, the processor circuitry to detect the sound by:
performing a comparison of a phase of a portion of the first vibration signal to a phase of a corresponding portion of the second vibration signal; and
detecting the sound when the phase of the portion of the first vibration signal is out-of-phase relative to the phase of the corresponding portion of the second vibration signal; and
control a user device based on the detection of the one or more of the sound or the motion.

8. The apparatus of claim 7, wherein the portion of the first vibration signal is a first portion and the processor circuitry is to:
perform a comparison of a phase of a second portion of the first vibration signal to a phase of a corresponding portion of the second vibration signal; and
detect the motion when the phase of the second portion of the first vibration signal is in-phase relative to the phase of the corresponding portion of the second vibration signal.

9. The apparatus of claim 7, wherein the processor circuitry is to control the user device by permitting access to a user application in response to the detection of the sound.

10. The apparatus of claim 9, wherein the processor circuitry is to control the user device by permitting access to the user application in response to the detection of both the sound and the motion.

11. The apparatus of claim 7, wherein the processor circuitry is to control the user device by denying access to a user application in response to the detection of the motion but not the sound.

12. The apparatus of claim 7, wherein the first bone structure is a first facial bone structure on a first side of a face of the user and the second bone structure is a second facial bone structure on a second side of the face of the user.

13. A non-transitory machine readable storage medium comprising instructions to cause processor circuitry to at least:
perform a comparison of phase characteristics of a first vibration signal and a second vibration signal, the first vibration signal output by a first sensor associated with a first bone structure of a user and the second vibration signal output by a second sensor associated with a second bone structure of the user;
identify sound data and motion data in the first vibration signal and the second vibration signal;
generate a modified signal including the sound data and not the motion data; and
perform an authentication of the user to one of enable or deny access to a user application based on the modified signal.

14. The non-transitory machine readable storage medium of claim 13, wherein the instructions cause the processor circuitry to:
detect the motion data but not the sound data in the first vibration signal and the second vibration signal; and
deny access to the user application based on the detection of the motion data but not the sound data.

15. A non-transitory machine readable storage medium comprising instructions to cause processor circuitry to:
perform a comparison of phase characteristics of a first vibration signal and a second vibration signal, the first vibration signal output by a first sensor associated with a first bone structure of a user and the second vibration signal output by a second sensor associated with a second bone structure of the user;
determine that the first vibration signal is associated with sound originating external to user; and
deny access to a user application.

16. A non-transitory machine readable storage medium comprising instructions to cause processor circuitry to:
perform a comparison of phase characteristics of a first vibration signal and a second vibration signal, the first vibration signal output by a first sensor associated with a first bone structure of a user and the second vibration signal output by a second sensor associated with a second bone structure of the user;
determine that the first vibration signal is associated with sound originating from the user based on (a) the comparison and (b) a difference in magnitude of the first vibration signal and the second vibration signal; and
enable access to a user application.

17. The non-transitory machine readable storage medium of claim 13, wherein the motion data is indicative of movement of a head of the user.

* * * * *